(12) United States Patent
Honeycutt et al.

(10) Patent No.: US 6,599,701 B1
(45) Date of Patent: Jul. 29, 2003

(54) IDENTIFYING ORGANISMS BY DETECTING INTRONIC NUCLEIC ACIDS

(75) Inventors: Rhonda J. Honeycutt, Carlsbad, CA (US); Michael McClelland, Encinitas, CA (US)

(73) Assignee: Clarity Biosciences, Inc., San Diego, CA (US)

( * ) Notice: Subject to any disclaimer, the term of this patent is extended or adjusted under 35 U.S.C. 154(b) by 10 days.

(21) Appl. No.: 09/645,055

(22) Filed: Aug. 23, 2000

Related U.S. Application Data

(60) Provisional application No. 60/150,977, filed on Aug. 25, 1999.

(51) Int. Cl.$^7$ ............................. C12Q 1/68; C12P 19/34; C07H 21/04
(52) U.S. Cl. ....................... 435/6; 435/91.2; 536/24.33; 536/24.3
(58) Field of Search .................. 536/24.33, 24.3; 435/91.2, 6

(56) References Cited

U.S. PATENT DOCUMENTS

| | | | |
|---|---|---|---|
| 4,458,066 A | 7/1984 | Caruthers et al. | 536/27 |
| 4,683,192 A | 7/1987 | Nishiyama | 430/567 |
| 4,683,202 A | 7/1987 | Mullis | 435/91 |
| 4,800,159 A | 1/1989 | Mullis et al. | 435/172.3 |
| 4,889,818 A | 12/1989 | Gelfand et al. | 435/194 |
| 4,965,188 A | 10/1990 | Mullis et al. | 435/6 |
| 5,250,203 A | 10/1993 | Denis et al. | 252/18 |
| 5,545,525 A | * 8/1996 | Montplaisir et al. | 435/6 |
| 5,849,492 A | 12/1998 | Rogan | 435/6 |

FOREIGN PATENT DOCUMENTS

| | | | |
|---|---|---|---|
| EP | 0545350 A | 12/1992 | G01N/33/531 |
| GB | 2310718 A | 9/1997 | C12Q/1/68 |
| WO | WO 89/07142 | 10/1991 | C12N/15/00 |
| WO | WO 00/03037 | 1/2000 | C12Q/1/168 |

OTHER PUBLICATIONS

Boucher, H. et al. (1996) *Gene* 189–196.
Brown, W. et al. (1982) *J Mol Evol* 18:225–239.
Brown, W.M. Evolution of Animal Mitochondrial DNA. In: *Evolution of genes and proteins*, ch. 4, pp. 62–81 (Ed. Nei Masatoshi and Richard Koehn), Sinauer Associates Inc., Sunderland, Massachusetts, 1983.
Donnelly, S.M. et al. (1999) *Microbiology* 145:1871–1882.
Everett, K. et al. (1999) *J of Bacteriology* 181(16):4734–4740.
Fulton, C. and Brown, A. (1997) *FEMS Microbiology Letters* 157:307–312.
Hanse, G. (1996) *J of Clinical Microbiology* 34(8):2049–2050.
Holst–Jensen, A. et al. (1999) *Mol Biol Evol* 16(1):114–126.
Johansen, S. (1991) *J DNA Sequence and Maping* 2:193–196.
McCullough, M. et al. (1999) *J of Clinical Microbiology* 37(2):417–421.
Neuveglise, C. et al. (1997) *Mol Ecology* 6:373–381.
Suh, S.–O., et al. (1999) *J Mol Evol* 48:493–500.
Tan, M.K. (1997) *J Mol Evol* 44:637–645.
Allen et al. (1989). *BioTechniques* 7:736–744.
Ausubel et al. In: *Curent Protocols in Molecular Biology*, John Wiley & Sons, NY, pp. 13.11.1–13.11.4 (1994).
Ausubel et al. *Moleculat Cloning of PCR Products*, in: Short Protocols in Molecular Biology, 3rd Ed. John Wiley & Sons, Inc. New York, pp. 15–32 (1997).
Barany et al. (1991). *PCR Meth Applic* 1:15–16.
Beaucage et al. (1981). *Tetrahedron Lett* 22:1859–1962.
Belcour et al. (1997). *Curr Genet* 31:308–317.
Berres et al. (1995). *Mycologia* 87:821–840.
Boerwinkle et al. (1989). *Proc Natl Acad Sci USA* 86:212–216.
Bretagne et al. (1995). *J Clin Micribiol* 33:1164–1168.
Brown et al. (1979). *Meth Enzymol* 68:109.
Cech. (1990). *Annu Rev Biochem* 59:543–568.
Caruthers. (1985). *Science* 230:281–285.
Dandliker et al. (1965). *J Exp Med* 122:1029.
Denhardt. (1966). *Biochem Biophys Res Commun* 23:641.
DeScenzo et al. (1994). *Phytopathol* 84:534–540.
Ehricht et al. (1997). *Eur J Biochem* 243:358–364.
Einsele et al. (1997). *J Clin Microbiol* 35:1353–1360.
Fahrlander et al. (1988). *Bio/Technology* 6:1165–1168.
Fodor et al. (1993). *Nature* (Lond) 364:555–556.
Fredricks et al. (1998). *Clin Microbiol* 36(10):2810–2816.
Garbelotto et al. (1993). *Can J Bot* 71:565–569.
Glass et al. (1995). *Applied and Environmental Microbiology* 61(4):1323–1330.
Goldman et al. (1982). *Electrophoresis* 3:24–26.
Henderson et al. (1986). *Clin Chem* 32:1637–1641.
Holland et al. (1991). *Proc Natl Acad Sci* (USA) 88:7276–7280.

(List continued on next page.)

*Primary Examiner*—Kenneth R. Horlick
*Assistant Examiner*—Joyce Tung
(74) *Attorney, Agent, or Firm*—Morrison & Foerster LLP

(57) ABSTRACT

The present invention provides novel methods for characterizing organisms by identifying the presence, absence, size or sequence polymorphism of intronic regions. The method involves selecting intronic regions from nuclear or organellar gene sequences that are useful for differentiating between and among taxonomic groupings of organisms. Such intronic regions can be analyzed directly or after amplification in a primer extension reaction. The amplification product is then analyzed by, for example, size fractionation, nucleotide sequencing or (RFLP). Intronic regions that contain an open reading frame encoding all or a portion of a protein can be used to generate antibodies to detect the presence or absence of the protein, which indicates the presence or absence of the intronic region. Methods of detecting an organism in a sample by detecting the presence or absence of one or more intronic regions also are provided using nucleic acid based or immunological based approaches. Kits are provided for practicing the methods of the invention.

11 Claims, 2 Drawing Sheets

OTHER PUBLICATIONS

Honeycutt et al. (1997). *Anal Biochem* 248:303–306.
Huse et al. (1989). *Science* 246:1275–1281.
Ieven et al. (1997). *Clin Microbiol Rev* 10:242–256.
Kreuzinger et al. (1996). *Applied and Environmental Microbiology* 62(9);3432–3438.
Lai et al. (1997). *Systematic Botany* 22(3):519–528.
Loffler et al. (1996). *QIAGEN News* 4:16–17.
MacDonald et al. (1990). *Plant Disease* 74:655–659.
Maclean et al. (1993). *Adv Plant Path* 10:207–244.
Makimura et al. (1994). *Med Microbiol* 40:358–364.
Manulis et al. (1994). *Phytopathol* 84:98–101.
Marshall. (1983). *Electrophoresis* 4:269–272.
Michel et al. (1995). *Annu Rev Biochem* 64:435–461.
Miller et al. (1988). *Phytopathol* 78:1516.
Mueller et al. (1997). *Histochem Cell Biol* 108:431–437.
Muller et al. (1998). *J Clin Microbiol* 36(6):1625–1629.
Nrang et al. (1979). *Meth Enzymol* 68:90.
Oellerich. (1980). *J Clin Chem Clin Biochem* 18:197–208.
Paquin et al. (1997). *Curr Genet* 31:380–395.
Reddy et al. (1993). *Mol Cell Probes* 7:121–126.
Rigby et al. (1977). *J Mol Biol* 113:237.
Rubenstein. (1972) *Biochem Biophys Res Commun* 47:846–851.
Sellem et al. (1997). *Mol Evol Biol* 14:518–526.
Smith et al. (1996). *Genome Res* 6:454–462.
Swaminathan et al. In *Diagnostic Molecular Microbiology, Principles and Applications*, DH Persing et al. eds., ASM Press, Washington, DC, pp. 26–50. (1993).
Tang et al. (1997). *Clin Chem* 43:2021–2038.
Tegelstrom. (1987). *Electrophoresis* 7:226–229.
Urdea et al. (1991). *Nucleic Acids Symp Ser* 24:197–200.
Van Belkum et al. (1994). *Clin Infect Dis* 18:1017–1019.
Verweij et al. (1995). *J Clin Pathol* 48:474–476.
Walker et al. (1992). *Nucleic Acids Res* 20:1691–1696.
Wang et al. (1998). *Medical Mycology* 36(3):153–164.
Wisdom. (1976). *Clin Chem* 22(8):1243–1255.
Yamakami et al. (1996). *J Clin Microbiol* 34:2464.
Zambino et al. (1998). *Proc Finnish Forest Res Instit* 712:297298.

* cited by examiner

US 6,599,701 B1

IDENTIFYING ORGANISMS BY DETECTING INTRONIC NUCLEIC ACIDS

This application claims priority under 35 U.S.C. §119(e) from provisional application No. 60/150,977, filed Aug. 25, 1999, the contents of which are incorporated herein by reference.

FIELD OF THE INVENTION

This invention relates to the field of nucleic acid and protein detection and, more specifically, to the rapid and accurate identification of organisms by detecting differences in nuclear and organellar introns.

BACKGROUND OF THE INVENTION

Microorganisms are the cause of damaging infections in both plants and animals. About 1.3% of patients admitted to hospitals in the U.S. have positive fungal cultures. In particular, Candida albicans is one of the most frequently observed pathogens in immunocompromised patients. Most individuals are colonized with C. albicans as a commensal organism, and when the individual becomes immunocompromised, the organism can establish an infection. Systemic Candida infections extend hospital stays and contribute to increased mortality.

There is a need for epidemiological and diagnostic tools to detect infectious microorganisms in situations where they are hard to distinguish or where the nature of the agent is still under investigation. This is particularly true in fungal diseases where considerable effort has gone into studying and combating such diseases in immunocompromised human patients and in diseases of crops.

Epidemiological and diagnostic tools for classifying plant infecting and mammalian infecting fungi have been used to identify the origin of fungal infections and to track the progression of disease after treatment with antifungal drugs. In the case of mammalian fungal pathogens, there are at least 19 species of Aspergillus and at least seven species of Candida that cause infection. Almost all the "species" in these genera are defined solely by morphological and nutritional characteristics. These tests are laborious and expensive and have not provided sufficient discrimination to date to classify all infectious organisms.

A variety of detection and identification methods have more recently been developed for detecting Candida albicans, including the germ tube test, carbohydrate assimilation test, antigen test, serology, fluorescein-conjugated lectin visualization, and nucleic acid detection by polymerase chain reaction (PCR). Despite these tests, current diagnosis of Candida continues to rely on differential culturing, because non-culture tests are costly, requiring multiple enzymatic or hybridization steps and, in the case of PCR, a series of different reaction cocktails and conditions. This additional work diminishes the throughput of a clinical laboratory and increases the chance of error.

There are no less than 30 genera of fungi involved in plant diseases and the relationships among these various species and genera of fungi is still not fully understood. Almost all the "species" in plant fungal genera are presently defined by morphological features or by host range. However, the lack of good morphological characters in fungi has led to often opposing classifications based on host plants, as for in "forma specialis," or other characters for sub-species groupings. Furthermore, in some cases, fungal morphological features can only be discerned when infections are well established on the plant host and symptoms are visible, or when the fungi are present in large enough quantities to be cultured from the plant. Thus, diagnostics of plant infecting fungi is at a rudimentary stage and early detection in asymptomatic plants is not possible using these methods.

Molecular-based methods have been applied to a very limited number of plant pathogenic fungi (reviewed by Swaminathan et al., in *Diagnostic Molecular Microbiology, Principles and Applications*, D H Persing et al. eds., ASM Press, Washington, D.C., pp 26–50 (1993)). For example, immunoassays have been devised for earlier detection of Pythium (Miller et al., *Phytopathol.* 78:1516 (1988)), Phytophthora and Rhizoctonia (MacDonald et al., *Plant Disease* 74:655–659 (1990)) and *Mycosphaerella fijiensis* (Novartis, AG Crop Protection Division, Basal Switzerland). Also, commercial kits are available and certified testing laboratories provide enzyme-linked immunoadsorbent assay (ELISA)-based assays for detection of some fungal species.

Furthermore, a variety of nucleic acid protocols have been used to detect plant pathogens, including plasmid content, pulsed field gel electrophoresis, nucleic acid hybridization, restriction digestion, and PCR (reviewed in Maclean et al., *Adv. Plant Path.*, 10:207–244 (1993); van Belkum et al., *Clin. Infect. Dis.*, 18:1017–1019 (1994); and Tang et al., *Clin. Chem.*, 43:2021–2038 (1997)). A few examples of the application of these approaches to fungal pathogens in plants include the arbitrarily primed PCR ("APPCR" or random amplified polymorphic DNA: "RAPD")—based identification for epidemiology and population studies of intersterility groups in *Heterobasidion annosum* (Garbelotto et al., *Can. J. Bot.*, 71:565–569 (1993)) and RAPD-based identification of pathogenic versus non-pathogenic isolates of *Fusarium oxysporum* formal specialis (f. sp.) dianthi (Manulis et al., *Phytopath.*, 84:98–101 (1994)).

In addition, probes developed from tandem repeat loci within satellite DNA have been used to detect polymorphisms among *Heterobasidion annosum* isolates (DeScenzo et al., *Phytopath.*, 84:534–540 (1994)).

Although each of these methods are useful, there currently is no single effective approach for detection and classification. Moreover, many of the methods require some foreknowledge of the particular species of organism likely to be present. It is apparent that a need exists for improved molecular methods that avoid the increased costs and reduced speed associated with present diagnostic and epidemiological tests for determining infection of plants and animals.

SUMMARY OF THE INVENTION

Accordingly, it is an object of the present invention to provide an approach to identify nucleic acid sequences and associated proteins that are useful for readily characterizing target organisms, such as differentiating between taxonomic groupings of target organisms, identifying the taxonomic group to which an organism belongs, etc. It also is an object of the present invention to use such nucleic acid sequences to rapidly and effectively identify organisms that are present in a sample. It is another object of the present invention to provide isolated nucleic acids comprising intronic regions useful in the methods of the invention. It is yet another object to provide kits suitable for practicing the methods of the invention.

To accomplish these and other objectives, there has been provided, according to one aspect of the present invention, a method for characterizing nuclear and organellar intronic regions that differ between or among various taxonomic groupings of organisms.

In one embodiment, an intronic region is selected from aligned nucleotide sequences of one or more gene homologs.

In another embodiment, a primer pair is generated for amplifying the intronic region and an amplified product is generated in a primer extension reaction. The amplified product from intronic regions of known organisms are analyzed to determine if the intronic region will be useful for characterizing unknown organisms. In one embodiment, the intronic region-specific primers flank more than one intron insertion site while in another embodiment, the intron region-specific primers flank a single intron insertion site.

In yet another embodiment, the intronic region is selected from gene sequences of organisms that reflect a broader taxonomic grouping than the taxonomic grouping of the target organisms sought to be characterized.

In still yet another embodiment, the target organisms sought to be characterized are from a single genus or very related genera and the organisms from which gene sequences are obtained are from different taxonomic classes or subclasses of organisms.

In further embodiments, the analysis of the amplified products from primer extension reactions include determining the presence or absence of the intronic region, the length of the intronic region, the nucleotide sequence of the intronic region, or restriction fragment length polymorphism. In some of these embodiments, the amplified product is detected by hybridizing with specific nucleic acid probes.

In yet a further embodiment, the nucleotide sequence of an intronic region identified from above is used to prepare intronic region-specific primers that are complementary to a sequence of nucleotides in the DNA of a particular target organism.

In an additional embodiment, intronic regions that contain an open reading frame encoding a protein (intronic region encoded protein: "IREP") are detected by generating specific antibodies to the protein or by detecting enzymatic activity of the protein.

The present invention also provides methods to detect the presence of a particular organism in a sample based on characterizing its intronic region sequences. In accordance with this aspect of the present invention, intronic region sequences are detected by nucleic acid detection approaches including primer extension, probe hybridization and other methods. In primer extension reactions, the intronic region-specific primers flank more than one intron insertion site while in another embodiment, the intron region-specific primers flank a single intron insertion site.

In other embodiments, the analysis of the amplified products from primer extension reactions include determining the presence or absence of the intronic region, the length of the intronic region, the nucleotide sequence of the intronic region, or restriction fragment length polymorphism. In some of these embodiments, the amplified product is detected by hybridizing with specific nucleic acid probes.

In yet another embodiment, intronic region-specific primers that are complementary to a sequence of nucleotides in the DNA of a particular target organism are used in primer extension at high stringency.

In accordance with another aspect of the present invention, an intronic region comprising all or a portion of an open reading frame is detected by detecting the encoded protein (IREP) using antibodies specific for the encoded protein or by detecting enzymatic activity characteristic of the protein.

The present invention also provides isolated nucleic acids, comprising an intronic region from a fungal gene, which can be used as a probe and to express the encoded protein.

The present invention also provides the amino acid sequences of fungal mitochondrial intronic region open reading frames that can be used to raise anti-IREP antibodies of the invention and can be expressed to determine an associated enzymatic activity.

The present invention further provides kits for practicing the methods of the invention.

Other objects, features and advantages of the present invention will become apparent from the following detailed description.

DETAILED DESCRIPTION OF THE INVENTION

Figure 1:
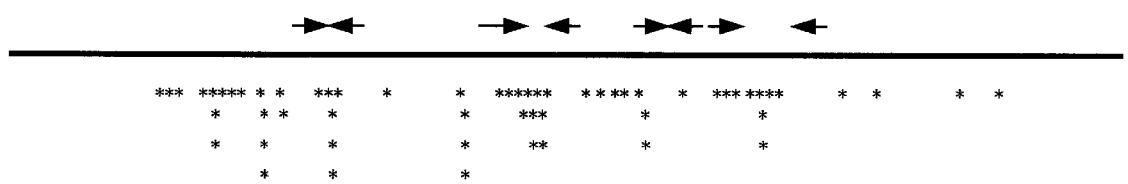
FIG. 1 is a schematic representation of the cytochrome oxidase subunit 1 (cox 1) gene showing the location of introns identified by alignment of the cox 1 gene from eleven fungal organisms. The solid horizontal line represents the aligned exons (1815 bases drawn to scale), while each asterisk below the line represents an intron insertion. Asterisks aligned in a column represent an intron at the same insertion site in the same gene sequence in multiple organisms. The opposed sets of arrows above the gene identify the locations of intronic region-specific primer pairs.

The present invention provides novel methods of analyzing nuclear or organellar intronic regions that are useful to distinguish between or among taxonomic groupings of organisms sought to be characterized (i.e., target organisms). The above methods can be applied to any organism that contains DNA having intronic regions, including fungi, protozoans and other members of the plant and animal kingdoms.

The method involves selecting an intronic region from a nucleotide sequence of one or more gene homologs. Such intronic regions can be selected by means well known in the art. The intronic regions are then analyzed in DNA of known organisms by a variety of nucleic acid detection methods such as primer extension reactions, separation of amplified products by molecular weight, nucleotide sequencing, or restriction fragment length polymorphism.

In primer extension, intronic region-specific primers suitable for amplifying intronic regions are synthesized and used to amplify the intronic regions in the target organism DNA, if present. The usefulness of a particular intronic region for differentiating between or among taxonomic groupings of target organisms is determined by analyzing the amplified products. Analysis is accomplished, for example, by detecting the presence or absence of the intronic region. Analysis also can be performed by detecting differences in length of the intronic region in the nucleic acid from different organisms (i.e., primer defined length polymorphism; PDLP) or differences in the sequence of the intronic region in the nucleic acid from different organisms (i.e., primer defined sequence polymorphism; PDSP). By analyzing a panel of intronic regions, a taxon-specific profile of intronic region differences or polymorphisms is identified that can differentiate between or among related species of organisms. Such polymorphisms are useful, for example, to identify all members of a genus or to identify different species of a single genus.

A. Definitions

Nucleotide: A monomeric unit of DNA or RNA consisting of a sugar moiety (pentose), a phosphate, and a nitrogenous heterocyclic base. The base is linked to the sugar moiety via the glycosidic carbon (1' carbon of the pentose) with the combination of base and sugar referred to as a nucleoside. When the nucleoside contains a phosphate group bonded to the 3' or 5' position of the pentose sugar, it is referred to as a nucleotide. A sequence of linked nucleotides is referred to herein as a "base sequence" or "nucleotide sequence," and their grammatical equivalents, and is represented herein in the conventional left to right orientation being 5'-terminus to 3'-terminus.

Nucleic Acid: A polymer of nucleotides, either single or double stranded.

Polynucleotide: A polymer of single or double stranded nucleotides. As used herein "polynucleotide" and its grammatical equivalents include the full range of nucleic acids. A polynucleotide will typically refer to a nucleic acid molecule comprising a linear strand of two or more deoxyribonucleotides and/or ribonucleotides. The polynucleotides of the present invention include primers, probes, RNA/DNA segments, oligonucleotides or "oligos" (relatively short polynucleotides), genes, vectors, plasmids, and the like.

Gene: A nucleic acid whose nucleotide sequence codes for an RNA or polypeptide. A gene can be either RNA or DNA. A gene also can include intervening segments known as introns.

Complementary Sequence of Nucleotides: A sequence of nucleotides in a single-stranded molecule of DNA or RNA that is sufficiently complementary to a sequence of nucleotides on another single strand of DNA or RNA such that the two strands can hybridize together.

Conserved Sequence of Nucleotides: A nucleotide sequence is conserved with respect to a preselected sequence if the nucleotide sequence can specifically hybridize to an exact complement of the preselected sequence.

Upstream: In the direction opposite to the direction of DNA transcription and, therefore, in a direction from 5' to 3' on the non-coding strand of the DNA, or from 3' to 5' on the mRNA or DNA coding strand.

Downstream: In the direction of DNA transcription and, therefore, in a 3' to 5' direction along the non-coding strand of the DNA or from 5' to 3' on the mRNA or DNA coding strand.

Hybridization: The pairing of substantially complementary nucleotide sequences (strands of nucleic acid) to form a duplex or heteroduplex through formation of hydrogen bonds between complementary base pairs. It is a specific, i.e., non-random, interaction between two complementary polynucleotides.

Hybridization Stringency: Refers to the conditions under which hybridization between two nucleic acid strands is conducted.

High stringency refers to conditions that permit hybridization of only those nucleic acid sequences that form stable hybrids in 0.018M NaCl at 65° C. High stringency conditions can be provided, for example, by hybridization in 50% formamide, 5×Denhardt's solution, 5× sodium chloride-sodium phosphate- Ethylenediaminetetraacetic acid buffer (SSPE buffer), 0.2% sodium dodecyl sulfate (SDS) at 42° C., followed by washing in 0.1×SSPE, and 0.1% SDS at 65° C.

Moderate stringency refers to conditions equivalent to hybridization in 50% formamide, 5×Denhardt's solution, 5×SSPE, 0.2% SDS at 42° C., followed by washing in 0.2×SSPE, 0.2% SDS, at 65° C.

Low stringency refers to conditions equivalent to hybridization in 10% formamide, 5×Denhardt's solution, 6×SSPE, 0.2% SDS, followed by washing in 1×SSPE, 0.2% SDS, at 50° C.

Recipes for Denhardt's solution and SSPE are well known to those of skill in the art as are other suitable hybridization buffers (e.g., Sambrook et al., supra, (1989)). For example, SSPE is pH 7.4 phosphate-buffered 0.18M NaCl. SSPE can be prepared, for example, as a 20×stock solution by dissolving 175.3 g of NaCl, 27.6 g of $NaH_2PO_4$ and 7.4 g ethylenediaminetetraacetic acid (EDTA) in 800 ml of water, adjusting the pH to 7.4, and then adding water to 1 liter. Denhardt's solution (Denhardt, *Biochem. Biophys. Res. Commun.*, 23:641 (1966)) can be prepared, for example, as a 50×stock solution by mixing 5 g Ficoll (Type 400, Pharmacia LKB Biotechnology, Inc., Piscataway, N.J.), 5 g polyvinylpyrrolidone, and 5 g bovine serum albumin (Fraction V; Sigma Chem. Co., St. Louis, Mo.) with 500 ml water and filtering to remove particulate matter.

In the case of PCR, high stringency refers to primer annealing temperatures that are from 0 to 5° C. less than the primer Tm. Moderate stringency refers to primer annealing temperatures that are from 5.1 to 10.0° C. less than the primer Tm. Low stringency refers to primer annealing temperatures that exceed 10.1° C. less than the primer Tm (e.g., 15° C.).

Intron: A non-protein coding region of DNA that is transcribed into a region of RNA that is removed during splicing together of protein coding regions ("exons") to form messenger RNA.

Intronic Region: DNA sequence comprising an entire intron and some or all of its adjoining upstream and downstream exons, or a portion of an intron with or without some or all of its adjoining upstream exon or some or all of its adjoining downstream exon. The intronic region can be present in nuclear DNA of eukaryotes as well as in organellar DNA from such organelles as mitochondria and chloroplasts and the like. Thus, mitochondrial intronic regions and chloroplastic intronic regions are examples of organellar intronic regions included within the meaning of intronic regions as used herein. Bacterial chromosomal DNA also can contain intronic regions.

Amplified Product: Copies of a portion of a DNA sequence and its complementary sequence, which copies correspond in nucleotide sequence to the original DNA sequence and its complementary sequence.

Complement: A DNA sequence that is complementary to a specified DNA sequence.

Primer Site: The segment of the target DNA to which a primer hybridizes.

Primer Extension Reaction: Any of a number of methods that result in the synthesis of a nucleotide sequence from a partially double stranded segment of nucleic acid. A variety of enzymes are known that can add nucleotides to the 3' end of the single stranded segment of the partially double stranded template.

Primer: A polynucleotide, whether purified from a nucleic acid restriction digest or produced synthetically, which is capable of acting as a point of initiation of nucleic acid synthesis when placed under conditions in which synthesis of a primer extension product complementary to a nucleic acid strand is induced, i.e., in the presence of nucleotides and an agent for polymerization such as DNA polymerase, reverse transcriptase and the like, and at a suitable temperature and pH.

Pair of Primers: A 5' upstream primer that hybridizes at the 5' end of the DNA sequence to be amplified and a 3' downstream primer that hybridizes at the 3' end of the sequence to be amplified.

Intronic Region-Specific Primers: A primer pair that amplifies at least one intronic region. The intronic region-specific primer sites can be located in the intron, adjacent upstream and/or downstream exon sequences, upstream or downstream non-adjacent exons or upstream or downstream introns (e.g., FIG. 2a) and any combinations thereof.

Homologous Intron: An intron that is present at the same insertion site in the same gene from different organisms without regard to the sequence of the intron.

Primer-Defined Length Polymorphisms (PDLP): Differences in the lengths of amplified DNA sequences due to insertions or deletions in an intronic region that is amplified.

Endonuclease or Restriction Endonuclease: An enzyme that cuts double-stranded DNA of a particular nucleotide sequence called a restriction site. The specificities of numerous endonucleases are well known and can be found in a variety of publications, e.g., Sambrook et al., supra, (1989). Endonucleases that produce blunt end DNA fragments by hydrolyzing a phosphodiester bond on both DNA strands at the same site as well as endonucleases that produce sticky ended fragments by hydrolyzing a phosphodiester bond on each strand of the DNA but at separate sites can be used for analysis of DNA sequence differences and for cloning DNA fragments.

Restriction Fragment Length Polymorphism (RFLP): A characterization of DNA nucleotide sequence based on the length of fragments generated when cleaved by a restriction endonuclease.

Primer-Defined Sequence Polymorphisms (PDSP): Differences in the sequences of amplified DNA in an intronic region of the amplified DNA sequence.

Taxon-Specific Intronic Polymorphisms: Differences between and among classical taxonomic groups of organisms. These are based on the polymorphisms defined by the presence, absence of an intron as well as by PDLP and PDSP. As used herein, taxa includes classical groupings such as genus and species, as well as nonclassical groupings which include, for example, species complex, race, subspecies, formal specialis, pathovar, biovar, cultivar and the like.

Target Organisms: Organisms sought to be characterized and whose nucleic acid is used in amplification reactions with intronic region-specific primers to determine polymorphisms based on presence, absence, length or sequence of the intronic region.

Antibody: Any of a large number of proteins of high molecular weight that are produced normally by specialized B type lymphocytes after stimulation by an antigen and act specifically against the antigen in an immune response. Antibodies typically consist of four subunits including two heavy chains and two light chains-also called immunoglobulins. As used herein, antibody includes naturally occurring antibodies as well as non-naturally occurring antibodies such as domain-deleted antibodies, single chain Fv antibodies and the like.

Immunological Binding Reagent: Any type of molecule that is useful to detect a first antibody molecule that binds to a target antigen. An immunological binding reagent can include a labeled second antibody specific for the first antibody or may include avidin or streptavidin when the first antibody is conjugated to biotin. An immunological binding reagent also can be a chemical that has binding specificity for an antibody or other protein.

B. Selecting Intronic Regions Useful for Identifying Organisms

Intronic regions can be selected from sequences obtained from publicly available gene databases such as GOBASE (University of Montreal, Montreal, Canada; http://megasun.bch.umontreal.ca/gobase/), GenBank (National Center for Biotechnology Information, Washington, D.C.; http://ncbi.nlm.nih.gov/), EMBL (EMBL Outstation-European Bioinformatics Institute, Cambridge, UK, http://www.ebi.ac.uk/embl) or DDBJ (National Institute of Genetics, Mishima, Japan, http://www.ddbj.nig.ac.jp).

The sequences should be obtained from organisms that are at least broadly taxonomically related to the target organisms sought to be characterized. Such sequences are preferably from organisms within the same kingdom. The gene sequence of the host genome, be it plant, human, or other animal, should be included for comparison, particularly when the sample to be analyzed includes nucleic acid from both the target organism and the host organism (e.g., a blood sample suspected to be infected). For example, if the target organism is a yeast, the gene sequences used to select intronic regions are preferably from fungi.

In fungi, the most conserved mitochondrial genes are the cytochrome oxidase subunit 1 (cox1) the apocytochrome b (cob), and the ribosomal genes. Sequences of these and other mitochondrial genes are available in GOBASE, which includes, for example, the sequences of mitochondrial genes, cob 1, cox 1, cox2, cox3, nad1, nad2, nad3, nad4, nad5, atp6, and atp9. These sequences are from subclasses of fungi that have been most extensively studied. Mitochondrial introns have been identified in cob, cox1, cox2, nad1, nad5, and other genes.

In addition to public databases, genes with intronic regions also can be cloned and their nucleotide sequence determined (Example 8). Methods for cloning and sequencing genes are well known, including the Sanger dideoxy mediated chain-termination approach and the Maxam-Gilbert chemical degradation approach. These and other nucleic acid sequencing methods are described, for example, in Sambrook et al., Molecular Cloning: A Laboratory Manual, Cold Spring Harbor Laboratory (1989) (chapter 13). Nucleic acid sequencing can be automated using a number of commercially available instruments.

An intronic region can be selected for its ability to differentiate between and among various taxonomic groupings of organisms by a variety of means. An intronic region can be identified, for example, by locating the nucleotide sequence that is present between intronic splice sites in a gene, or aligning the exon(s) of a gene from the nucleotide sequences of at least two organisms that encode the specified gene. Intronic regions also can be identified by comparing cDNA sequence to genomic sequence and by statistical methods to identify sequence motifs and codon usage characteristic of introns. These methods are well known in the art.

When aligning sequences to identify an intronic region, it is important to select gene sequences that contain at least one exon and at least one intron. Sequences without an intron can be used to define a consensus sequence for intronic region-specific primers, but a minimum of two sequences, of which at least one contains an intron, is necessary to identify an intronic region for analysis. The selected gene sequences are aligned according to the exon sequence. Alignment can be accomplished manually or more preferably with a publicly available computer sequence alignment program such as MAP (multiple alignment program) accessible at Baylor College of Medicine (BCM, Houston, Tex.)) Search Launcher website (http://www.hgsc.bcm.tmc.edu/SearchLauncher/; Smith et al., *Genome Res.*, 6:454–462 (1996)). Alignments can be made from GOBASE by separate downloading of exons and introns, while GenBank accession is usually available as a single genomic sequence.

Once the exons are aligned, the identity and insertion site of the intron can be determined by visual inspection and an intronic region selected. For example, all the exons of a specified gene (e.g., cox1) for a given organism can be downloaded (e.g., from GOBASE), and fused (in order) into a single file. This process is repeated for each additional organism to be compared. The sequences are then aligned using MAP and the resulting alignments of exons are compared to the genomic sequence to locate intronic insertion sites. In some cases, the intronic sequence is available for confirmation or the exon:intron boundaries are annotated in the database (e.g., GenBank). Primers are then derived to enable detection of intronic polymorphisms.

In some situations, analysis of a single intronic region in the nucleic acid of a target organism will be sufficient to differentiate the organism between or among a particular taxonomic grouping of organisms. More typically, discrimination will require that multiple intronic regions be identified and analyzed. Multiple intronic regions can be identified, for example, by aligning homologous sequences in one or more gene homologs. Multiple intronic regions can be detected using a single primer pair that flanks more than one intron. A homologous intron is one that is present at the same insertion site in the same gene from different organisms without regard to the sequence of the intron). Homologous introns can have the same nucleotide sequence or can have different nucleotide sequences. Such introns are particularly useful for identifying organisms at the subspecies level.

A total of 38 unique intron insertions sites are present in approximately 1400 of the 1800 bases in the consensus alignment of exons from all cox1 genes currently known in fungi. Thus, the cox1 gene provides a variety of mitochondrial intronic regions to select from a single alignment of sequences (Example 1).

C. Intronic Region-specific Primer Design and Preparation

Intronic regions selected as described herein are evaluated for their use in differentiating between or among selected taxonomic grouping of organisms by, for example, primer extension reactions using intronic region-specific primers. As used herein, intronic region-specific primers refer to a primer pair that is useful for amplifying at least a portion of one intron (i.e., an intronic region). Each primer is complementary to a primer site located in the intron, adjacent upstream and/or downstream exon sequences, upstream or downstream non-adjacent exons or upstream or downstream introns (e.g. FIG. 2a) and any combinations thereof The primer sites are preferably located in conserved sequences.

The intronic region-specific primer sites are generally located upstream and downstream of the intronic region with the 3' end of each primer situated toward the intron insertion site. In this way, the DNA polymerase in the primer extension reaction will generate a copy of the intronic region if it is present in the DNA template.

A primer is preferably single stranded for maximum efficiency, but may alternatively be in double stranded form. If double stranded, the primer is first treated to separate it from its complementary strand before being used to prepare extension products. Preferably, the primer is a polydeoxyribonucleotide. The primer must be sufficiently long to prime the synthesis of extension products in the presence of the agents for polymerization. The exact lengths of the primers will depend on many factors, including temperature and the source of primer.

The primers described herein are selected to be "substantially" complementary to the different strands of each specific sequence to be synthesized or amplified. This means that the primer must be sufficiently complementary to hybridize relatively specifically with its intended primer site in the target template strand. Therefore, the primer sequence may or may not reflect the exact sequence of the template. For example, a non-complementary nucleotide fragment can be attached to the 5' end of the primer, with the remainder of the primer sequence being substantially complementary to the strand. Such non-complementary fragments typically contain an endonuclease restriction site. Alternatively, non-complementary bases or longer sequences can be interspersed into the primer, provided the primer sequence has sufficient complementarity overall with the sequence of the strand to be synthesized or amplified to non-randomly hybridize therewith and thereby form an extension product under polynucleotide synthesizing conditions.

An intronic region-specific primer preferably includes at least about 15 nucleotides, more preferably at least about 20 nucleotides. The primer preferably does not exceed about 30 nucleotides, more preferably about 25 nucleotides, although it can contain fewer nucleotides. Short primer molecules generally require lower temperatures to form sufficiently stable hybrid complexes with the template. Most preferably, the primer includes between about 20 to about 25 nucleotides. The length of the primer will vary inversely with the extent of conservation of the complementary exon sequence. The GC content of the primers should be about 50%.

Intronic region-specific primers are preferably complementary to a primer site located in a conserved region of the gene. Intronic region-specific primers that are based on aligned gene sequences are preferably complementary to a primer site that reflects a consensus of the aligned sequences. The priming or hybridizing region of intronic region-specific primers typically includes the 3'-most (3'-terminal) 15 to 30 nucleotide bases. The 3'-terminal priming portion of each primer is capable of acting as a primer to catalyze nucleic acid synthesis, i.e., initiate a primer extension reaction from its 3' terminus. One or both of the primers can additionally contain a 5'-terminal (5'-most) non-priming portion, i.e., a region that does not participate in hybridization to the preferred template.

The 3'-most base of the primer should be situated either in the first or second position within the codon reading frame so that the 3'-most base is not in a wobble position of a codon. The 3' codon also should be chosen so that there are no redundant bases in the 3'-most position of the primers among coding sequences typical of the kingdom or other taxonomic grouping from which the sequences are derived.

Any nucleotides that are not identical to the sequence or its complement are preferably not located at the 3' end of the primer. The 3' end of the primer preferably has at least two, preferably three or more, nucleotides that are complementary to primer site in the template DNA.

In situations where a gene sequence alignment provides multiple potential intronic regions, as in the fungal cox 1 mitochondrial gene, one may select only a few of the intronic regions for the ability to differentiate between or among the taxonomic groups of interest. Those intronic regions that arise more frequently in the aligned sequences and that exhibit length and/or sequence differences among the aligned sequences are preferred.

One consideration when selecting the location of primer sites is the size of the product produced by primer extension. For example, in one embodiment, the amplifying primer sites are in the exon sequence immediately adjacent to the intron insertion site of the gene. In this case, primer extension will result in a very small sized product (about the combined length of the two primers or so) if the template DNA lacks the intronic region and potentially a much larger product if the template DNA contains the intronic region.

In another approach, the amplifying primers can be located sufficiently far away from the intron insertion site, for example in a non-flanking exon. In this case, primer extension will generate a larger product than in the case when the primer sites directly flank the intronic region. The intronic region-specific primer sites also can be located sufficiently far apart such that they span more than one intron insertion site. In this way, amplification by primer extension can generate a product that contains multiple intronic regions. Although this may complicate the analysis of each intronic region somewhat, this approach has the potential to detect intronic region insertions that were not predicted based on known gene sequence results (e.g., FIG. 2A).

Thus, the choice of primer site can affect the size of the product(s) that are produced in a primer extension reaction. Depending on the choice of nucleic acid analysis one can select intronic region-specific primer sites that will produce a particular sized product suited for the analysis method chosen.

Primers can be prepared using a number of methods, including phosphotriester and phosphodiester methods or automated embodiments thereof. The phosphodiester and phosphotriester methods are described in Cruthers, *Science*, 230:281–285 (1985); Brown et al., *Meth. Enzymol.*, 68:109 (1979); and Nrang et al., *Meth. Enzymol.*, 68:90 (1979). In one automated method, diethylphosphoramidites which can be synthesized as described by Beaucage et al., *Tetrahedron letters*, 22:1859–1962 (1981) are used as starting materials. A method for synthesizing primer oligonucleotide sequences on a modified solid support is described in U.S. Pat. No. 4,458,066.

D. Target Organisms and Isolation of Nucleic Acid

Primer extension reactions are preferably performed using purified DNA from the target organism. Isolation of DNA from cells is routine in the art and there are numerous sources of nucleic acid isolation protocols suited for microorganisms such as bacteria and fungi including mammalian cells (e.g., Sambrook et al., supra, (1989)). Primer extension reactions also can be performed using DNA that has not been purified but is accessible to the primer. The DNA can be accessible naturally in the sample or can be made accessible following one or more processing steps.

Isolation of fungal DNA can be accomplished by grinding spores in the presence of diatomaceous earth using a Savant grinding instrument (BIO 101, San Diego, Calif.) followed by RNAse treatment, phenol:chloroform extraction, and ethanol precipitation (Zambino et al., *Proc. Finnish Forest Res. Instit.*, 712:297–298 (1998)). Although this method is somewhat time-consuming, the yield and purity are sufficient in PCR with multiple sets of primers.

Other methods for fungal DNA extraction include, Reddy et al., *Mol. Cell Probes*, 7:121–126 (1993); Bretagne et al., *J. Clin. Microbiol.*, 33:1164–1168 (1995); Verweij et al., *J. Clin. Pathol.*, 48:474–476 (1995); Makimura et al., *Med. Microbiol.*, 40:358–364 (1994); Ausubel et al. in: *Current Protocols in Molecular Biology*, John Wiley & Sons, NY, pp. 13.11.1–13.11.4 (1994)). Commercial kits such as QIAAMP® (QIAGEN, Inc., Chatsworth, Calif.: Loffler et al., QIAGEN News, 4:16–17 (1996) and EASY-DNA® (Invitrogen, Inc., Carlsbad, Calif.) also are available.

Target organisms suitable for identification of intronic regions and for detection by the method disclosed herein include, for example, members of the Eucaryota (including Euglenozoa: trypanosoma) and Eucaryote Crown Group, subclasses of Fungi/Metazoa Group (Ascomycota, Basidiomycota, Oomycota, Chytidiomycota, and Zygomycota), Avelolata (e.g. Toxoplasma), Viridiplantae (e.g. achloric algae) and various other taxonomic grouping described in the NCBI Taxonomy database (http://www.ncbi.nlm.nih.gov/Taxonomy/tax.html).

Important fungal genera include, for example, Aspergillus, Candida, Coccidiodes, Cryptococcus, Histoplasma, Blastomyces, Cladosporium Fusarium, Tilletia, Puccinia, Septoria, Botrytis, Pyrenophora, and Gaeumannomyces.

E. Identifying Intronic Regions

Types of Intronic Regions

Introns can be classified as either Group I and Group II according to genomic intronic classification (reviewed in Cech, *Annu. Rev. Biochem.*, 59:543–568 (1990); and Perlman et al., *Intervening Sequences in Evolution and Development*, E. M. Stone and R. J. Schwartz, eds., Oxford Univ. Press, New York (1990)). The groups are distinguished by nucleotide sequence motifs and conserved secondary structure. A fungal species may contain both Group I and Group II introns and the number of introns varies widely between species.

Group I introns are more common in fungal mitochondria, range in length between 200 and 3000 bases, and may contain zero, one, or two open reading frames (ORFs) (Cech, supra, (1990)). Some of these ORFs encode proteins of known function including endonucleases and maturases, each having conserved amino acid motifs. Group I ORFs are also mobile elements (Sellem et al., *Mol. Evol. Biol.*, 14:518–526 (1997)).

Group II introns, which are found in fungal mitochondria and more commonly in plant chloroplasts range in length from 900 to 2500 bases. Such introns may contain ORFs encoding for reverse transcriptases (Michel, et al., *Annu. Rev. Biochem.*, 64:435–461 (1995)).

Optional introns are those which are present or absent in the same gene from different species of an organism. Fungi as opposed to insects and other animals have size differences in the mitochondrial genomes which are due in part to the presence of optional introns, and to a lesser extent by intergenic sequences and variation in coding capacity (Belcour et al., *Curr. Genet.*, 31:308–317 (1997)). Introns inserted at identical positions in homologous genes in unrelated species are considered homologous introns even though the intron sequences vary widely.

The insertion positions of some mitochondrial introns are highly conserved as in the cox1gene near amino acid 240 where homologous introns have been found in the fungi, *S. cerevisiae, P. anserina, Spizellomyces punctatus, Rhizophus stolonifer*, the liverwort *Marchantia polymorpha*, and the plant *Peperomia polybotrya* (Paquin et al., *Curr. Genet.*, 31:380–395 (1997)). Homologous introns also can be optional.

Intronic regions can include Groups I and II type introns as well as optional introns. Selected intronic regions are evaluated to determine their usefulness in differentiating between or among target organisms can be detected in nucleic acid of known organisms by a variety of methods. Such methods include analysis of nucleic acid from the target organism which can be detected directly by, for example, probe hybridization, cloning and sequencing or by analysis of amplified product from primer extension. Primer extension methods are preferred.

Primer Extension and Signal Amplification Methods

The intron-amplifying primers are used to amplify products from target DNA in a primer extension reaction. A variety of primer extension reactions can be used with the present methods. Non PCR amplification methods include ligase chain reaction (LCR: Barany et al., *PCR Meth. Applic.*, 1:15–16 (1991)), self-sustained sequence replication (SSR: Muller et al., *Histochem. Cell Biol.*, 108:431–437 (1997)), also known as nucleic acid sequence-based amplification: NASBA) and its new derivative, cooperative amplification of templates by cross-hybridization (CATCH: Ehricht et al., *Eur. J. Biochem.*, 243:358–364 (1997)), transcript-based amplification system (AMPLISCRIPT®, Kaylx Biosciences, Nepean, Ontario Canada), replicatable RNA reporter systems based on the Q beta replicase, hybridization-based formats such as strand-displacement amplification (SDA: Becton-Dickinson, Franklin Lakes, N.J.; Walker et al. *Nucleic Acids Res.*, 20:1691–1696 (1992)), and chip-based microarrays such as Affymetrix GeneChip (Fodor et al., *Nature*, (Lond) 364:555–556 (1993)).

Signal amplification methods also can be used to enhance detectability such as with the use of compound probes (Fahrlander et al., *Bio/Technology*, 6:1165–1168 (1988)) or branched probes (Chiron Corp., Emeryville, Calif.; Urdea et al., *Nucleic Acids Symp. Ser.*, 24:197–200 (1991)) as is well known in the art.

Primer extension by PCR is performed by combining one or more primers with the target nucleic acid and a PCR buffer containing a suitable nucleic acid polymerase. The mixture is thermocycled for a number of cycles, which is typically predetermined, sufficient for the formation of a PCR reaction product, thereby enriching the sample to be assayed for the presence, absence, size polymorphism or sequence polymorphism associated with a particular intronic region. Protocols for PCR are well known in the art (e.g., U.S. Pat. Nos. 4,683,192, 4,683,202, 4,800,159, and 4,965, 188) and are available from a variety of sources (e.g., PCR Technology: *Principles and Applications for DNA Amplification*, H. Erlich, ed., Stockton Press, New York (1989); and PCR Protocols: *A Guide to Methods and Applications*, Innis et al., eds., Academic Press, San Diego, Calif. (1990)).

PCR is typically carried out by thermocycling, i.e., repeatedly increasing and decreasing the temperature of a PCR reaction admixture within a temperature range whose lower limit is about 30 degrees Celsius (30° C.) to about 55° C., and whose upper limit is about 90° C. to about 100° C. Increasing and decreasing the temperature can be continuous, but is preferably phasic with time periods of relative temperature stability at each of the temperatures favoring polynucleotide synthesis, denaturation and hybridization. Thus, the PCR mixture is heated to about 90–100° C. for about 1 to 10 minutes, preferably from 1 to 4 minutes. After this heating period, the solution is allowed to cool to about 54° C., which is preferable for primer hybridization. The synthesis reaction may occur at room temperature up to a temperature above which the polymerase (inducing agent) no longer functions efficiently. Thus, for example, if Taq DNA polymerase is used as inducing agent, the temperature is generally about 70° C. The thermocycling is repeated until the desired amount of amplified product is produced.

A single intronic region-specific primer pair can be used in each amplification reaction. Alternatively, additional primers from other primers pairs can be included in the reaction. The primers are generally added in molar excess over template DNA. The conditions of the PCR are adjusted depending on a number of factors, including the degree of mismatch, the GC content of the primer, the length of the primer factors affecting PCR conditions, melting temperature of the primer, and product length and placement within the target sequence. Adjustments in the concentrations of the reaction components, especially magnesium concentration, can be used to enhance the conditions for PCR.

The PCR buffer contains the deoxyribonucleoside triphosphates (i.e., polynucleotide synthesis substrates) dATP, dCTP, dGTP, and dTTP and a polymerase, typically thermostable, all in amounts sufficient for the primer extension (i.e., polynucleotide synthesis) reaction. An exemplary PCR buffer comprises the following: 50 mM KCl; 10 mM Tris-HCl at pH 8.3; 1.5 mM $MgCl_2$; 0.001% (wt/vol) gelatin, 200 microMolar ($\mu$M) dATP, 200 $\mu$M dTTP, 200 $\mu$M dCTP, 200 $\mu$M dGTP, and 2.5 units Thermus aquaticus (Taq) DNA polymerase I (U.S. Pat. No. 4,889,818) per 100 microliters ($\mu$L) of buffer.

The inducing agent may be any compound or system which will function to accomplish the synthesis of primer extension products, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, such as heat-stable enzymes that facilitate combination of the nucleotides in the proper manner to form the primer extension products complementary to each nucleic acid strand. Generally, the synthesis will be initiated at the 3' end of each primer and proceed in the 5' direction along the template strand, until synthesis terminates, producing molecules of different lengths. There may be inducing agents, however, which initiate synthesis at the 5' end and proceed in the above direction, using the same process as described above. Intronic region-specific primers suitable for such inducing agents can be designed using the principles elaborated above for inducing agents that extend from the 3' end.

The PCR reaction can advantageously be used to incorporate into the product a preselected restriction site useful in later cloning and sequencing the amplified product. This can be accomplished by synthesizing the primer with the restriction site in the 5' end of the primer.

Nucleic acid from known organisms or products produced therefrom by primer extension reactions with intron-amplifying primers are analyzed to determine if the intronic region is present, absent, or varies by size (PDLP) and/or sequence in the DNA of target organisms. Primer-Defined Sequence Polymorphisms (PDSP) refer to differences in the sequences of amplified DNA in an intronic region of the amplified DNA sequence.

The amount of amplified nucleic acid product needed for analysis varies with the method chosen. Generally, about 1 to about 500 ng of amplified DNA product is required. As discussed above, a preferred primer extension method is PCR.

Fractionation of amplified products by size also is useful to evaluate differences in the length of the amplified intronic regions, referred to herein as a primer-defined length polymorphism (PDLP). PDLPs result, for example, from insertions or deletions in an intronic region. To detect PDLPs, the amplified DNA sequence is located in a region containing insertions or deletions of a size that is detectable by the chosen method. The amplified DNA sequence should be of a size that is readily resolved by the method chosen.

The presence or absence of the intronic regions in a target DNA is typically determined by analyzing the amplified nucleic acid products of the primer extension by size using standard methods, for example, agarose gel electrophoresis, polyacrylamide gel electrophoresis, capillary electrophoresis, pulsed field electrophoresis, and denatured gradient gel electrophoresis (DGGE). Non size based method include, for example, single stranded conformational polymorphism (SSCP). All of these methods are well known in the art (e.g., Sambrook et al., supra, (1989) (6.3–6.6); Nucleic Acid Electrophoresis (D. Teitz, ed.), Springer Verlag, N.Y. (1998).

DNA electrophoresis involves separation, usually in a supporting medium, by size and charge under the influence of an applied electric field. Gel sheets or slabs, e.g., agarose, agarose-acrylamide or polyacrylamide, are typically used for nucleotide sizing gels. Nucleic acid products of about 20 bp to >10,000 bases in length can be optimally resolved in the above electrophoretic methods in combination with different types of agarose. Nucleotide sequences which differ in length by as few as 3 nucleotides (nt), preferably 25 to 50 nt, can be distinguished by electrophoresis. Sequences as long as 800 to 2,000 nt, which differ by at least about 50 nt, also are readily distinguishable.

Preparation and staining of analytical nucleic acid electrophoretic gels is well known. For example, a 3% Nusieve 1% agarose gel which is stained using ethidium bromide is described in Boerwinkle et al., *Proc. Natl. Acad. Sci.* (USA), 86:212–216 (1989). Detection of DNA in polyacrylamide gels using silver stain is described in Goldman et al., *Electrophoresis*, 3:24–26 (1982); Marshall, *Electrophoresis*, 4:269–272 (1983); Tegelstrom, *Electrophoresis*, 7:226–229 (1987); and Allen et al., *BioTechniques*, 7:736–744 (1989). Nucleic acid also can be labeled with an isotope such as $^{32}P$ and detected after gel electrophoresis by autoradiography.

Size markers can be run on the same gel to permit estimation of the size of the amplified products or their restriction fragments. Comparison to one or more control sample(s) can be made in addition to or in place of the use of size markers. The size markers or control samples are usually run in one or both the lanes at the edge of the gel, and preferably, also in at least one central lane. In carrying out the electrophoresis, the DNA fragments are loaded onto one end of the gel slab (commonly called the "origin") and the fragments separated by electrically facilitated transport through the gel, with the shortest fragment electrophoresing from the origin towards the other (anode) end of the slab at the fastest rate. An agarose slab gel is typically electrophoresed using about 5–15 volts/cm of gel for 30 to 45 minutes. A polyacrylamide slab gel is typically electrophoresed using about 200 to 1,200 volts for 45 to 60 minutes.

Tables 1 and 2 in Example 3, summarize the results of size analysis of PCR amplified products by agarose gel electrophoresis. In this example, intronic region-specific primer pairs for detecting multiple intronic regions of the cox 1 gene were used to amplify product in template DNA from several species of the genus Candida and other fungi. Intron polymorphisms were identified between members of the genus Candida as differences in size as well as the absence of the intron.

In cases where hybridization assays of multiple target organism genomes are desired to be performed simultaneously using the same intronic region-specific probes, it would be convenient to perform such hybridizations in an array format. Such assay formats and minaturizations thereof, i.e. microchip assays, are well known in the literature and could easily be adapted for the assays described herein. For example, see PCT WO 00/03037, which describes screening arrays of nucleotides using specific probes. After compilation of the intronic region profile for a given taxonomic group, the nucleotide sequences corresponding to the intronic regions of the different organisms belonging to the taxonomic group can be used in a microarray format on a microchip to perform simultaneous hybridization studies with various probes or sequences from unknown organisms.

Alternatively, such assay formats can be designed for use to study hybridization of an array of intronic region-specific sequences with a single target organism genome, or an array of the protein products derived from the translation of intronic sequences of unknown organisms, or an array of antibodies to such protein products, or combinations thereof in two-dimensional arrays. Such hybridization microarray assays can easily be performed using a variety of known microchip assay formats and techniques.

Sequencing Analysis

Analysis of nucleic acid from known target organisms or products produced therefrom by primer extension as described herein also can include analysis of the sequence of the amplified intronic region including an adjoining exon of the target template DNA. Intronic region sequence as well as intronic region size can be determined by cloning and sequencing the intronic region. For example, amplified products such as from a PCR can be directly cloned by a variety of methods well known in the art (e.g., Ausubel et al., *Molecular cloning of PCR products*, in: Short Protocols in Molecular Biology, 3rd Ed. John Wiley & Sons, Inc., New York, pp. 15–32 (1997)). Cloning of amplified products can be accomplished using "sticky ends" such as the TA cloning method or by "blunt end" cloning approaches. Alternatively, intronic region-specific primers can be designed with endonuclease restriction sites at the 5' end of the primer which are designed for cutting and insertion into a specified cloning vector. Kits are commercially available for cloning amplified products such as produced in a PCR (e.g., Invitrogen, Inc., San Diego, Calif.). Cloned intronic regions of the cox1 mitochondrial gene from fungi are provided in Example 8.

Methods for sequencing genes are well known, including the Sanger dideoxy mediated chain-termination approach and the Maxam-Gilbert chemical degradation approach. These and other nucleic acid sequencing methods are described, for example, in Sambrook et al., supra, (1989) (chapter 13). Nucleic acid sequencing can be automated using a number of commercially available instruments.

Amplified products also can be directly sequenced without cloning the product (e.g., Sambrook et al., supra, (1989) (14.22–14.29)). Amplified products that have been purified, for example, by gel electrophoresis, are suitable for direct sequencing (id.).

Differences in the sequence of amplified products produced by primer extension with intronic region-specific primers also can be analyzed by RFLP. Direct sequencing is preferred over RFLP. However, RFLP analysis of amplified products from different DNA target templates can provide a screening tool for detecting sequence differences of similar sized products.

Restriction enzymes for performing RFLP are available commercially from a number of sources including Sigma Chemical Co. (St. Louis, Mo.), Bethesda Research Labs (Bethesda, Md.), Boehringer-Manheim (Indianapolis, Ind.) and Pharmacia & Upjohn (Bridgewater, N.J.). Endonucleases are chosen so that by using a plurality of digests of the amplified sequence, preferably fewer than five, more preferably two or three digests, the amplified products can be distinguished.

Intronic region-specific primers that are designed from aligned sequences are referred to herein are "first generation" primers because they are complementary to a consensus sequence. In contrast, when sequence information is obtained for amplified products, "second generation" intronic region-specific primers can be designed that are complementary to a specific primer site target sequence. Such second generation primers have increased specificity for particular organisms and can be designed to yield sizes of amplified intronic regions that are easier to detect. The products of the second generation primers may be detected as nucleic acids using methods described above. Second generation primers are preferred for the method of detecting an organism in a sample as discussed below.

Protein Detection Methods

Particular intronic regions that comprise all or a portion of an open reading frame (ORF) that encodes a protein (e.g., an enzyme) can be detected for their presence or absence in nucleic acid from known organisms by using antibodies specific for encoded protein or detection based on the enzymatic activity of the protein. Such enzymatic activity can include, for example, endonuclease, maturase or reverse transcriptase activity.

The expression of such an intronic region encoded protein ("IREP") by the organism, which is detected by an anti-IREP antibody, can be used to identify the organism. Using this approach, one can determine if the organism from which the protein is derived is living by incubating the sample under suitable conditions with one or more labeled amino acids precursors and determining if the label is associated with the intronic region protein.

Whether an intronic region encodes a protein can be detected using software programs that detect open reading frames based on all possible start and stop codons (e.g., MacVector v. 5.0.2). Example 8 discloses consensus sequences of five cox1 fungal mitochondrial introns, four of which contain an open reading frame. The sequence of the encoded ORF for the cloned cox1genes are provided in Example 8.

Monoclonal antibodies or polyclonal antisera raised against antigenic epitopes of the IREP are useful if the antigenic epitopes they detect differentiate between or among different taxonomic groupings of organisms. Binding of the anti-IREP antibody to the antigenic epitopes of the organism can be determined by methods well known in the art, including SDS-PAGE, Western Blotting, isoelectric focusing, 2-D gels, immunoprecipitation, epitope tagging, radioimmunoassay, enzyme-linked immunoadsorbent assay (ELISA), fluorescence and the like.;

An anti-IREP antibody is used in its broadest sense to include polyclonal and monoclonal antibodies, as well as polypeptide fragments of antibodies that retain a specific binding affinity for its target antigen of at least about $1 \times 10^5$ $M^{-1}$. One skilled in the art would know that antibody fragments such as Fab, $F(ab')_2$ and Fv fragments can retain specific binding activity for their target antigen and, thus, are included within the definition of an antibody herein. In addition, the term "antibody" as used herein includes naturally occurring antibodies as well as non-naturally occurring antibodies such as domain-deleted antibodies (Morrison et al., WO 89/07142) or single chain Fv (Ladner et al., U.S. Pat. No. 5,250,203). Such non-naturally occurring antibodies can be constructed using solid phase peptide synthesis, can be produced recombinantly or can be obtained, for example, by screening combinatorial libraries consisting of variable heavy chains and variable light chains as described by Huse et al., *Science*, 246:1275–1281 (1989).

Antibodies to IREPs can be prepared using a substantially purified IREP, or a fragment thereof, which can be obtained from natural sources or produced by recombinant DNA methods or chemical synthesis. For example, recombinant DNA methods can be used to express the intronic ORF sequence alone or as a fusion protein, the latter facilitating purification of the antigen and enhancing its immunogenicity.

If the IREP is not sufficiently immunogenic, it can be coupled to an immunogenic carrier molecule chemically or expressed as a fusion protein with such immunogenic carriers as bovine serum albumin or keyhole limpet hemocyanin (KLH). Various other carrier molecules and methods for coupling a non-immunogenic peptide to a carrier molecule are well known in the art (e.g., Harlow and Lane, "Antibodies: A Laboratory Manual," Cold Spring Harbor Laboratory Press (1988)).

Antisera containing polyclonal antibodies reactive with antigenic epitopes of the IREP can be raised in rabbits, goats or other animals. The resulting antiserum can be processed by purification of an IgG antibody fraction using protein A-Sepharose chromatography and, if desired, can be further purified by affinity chromatography using, for example, Sepharose conjugated with a peptide antigen. The ability of polyclonal antibodies to specifically bind to a given molecule can be manipulated, for example, by dilution or by adsorption to remove crossreacting antibodies to a non-target molecule. Methods to manipulate the specificity of polyclonal antibodies are well known to those in the art (e.g., Harlow and Lane, supra, (1988)).

A monoclonal antibody specific for the IREP can be produced using known methods (Harlow and Lane, supra, (1988)). Essentially, spleen cells from a mouse or rat immunized as discussed above are fused to an appropriate myeloma cell line such as SP2/0 myeloma cells to produce hybridoma cells. Cloned hybridoma cell lines can be screened using a labeled IREP to identify clones that secrete an appropriate monoclonal antibody. An IREP can be labeled as described below. A hybridoma that expresses an antibody having a desirable specificity and affinity can be isolated and utilized as a continuous source of monoclonal antibodies. Methods for identifying an anti-IREP antibody having an appropriate specificity and affinity and, therefore, useful in the invention are known in the art and include, for example, enzyme-linked immunoadsorbence assays, radioimmunoassays, precipitin assays and immunohistochemical analyses (e.g., Harlow and Lane, supra, (1988) (chapter 14)).

An anti-IREP antibody can be characterized by its ability to bind specifically to the organisms that express the particular IREP. Because organelles such as mitochondria are inside cells, the cells may need to be permeabilized to allow access of the antibody to the organelle. Methods to permeabilize cells are such as by treating with detergents are well known in the art (e.g., Harlow and Lane, supra, (1988)). Alternatively, a sample containing the organism can be subjected to protein purification methods to obtain a cell-free protein fraction suitable for antibody binding.

An anti-IREP antibody of the invention can be used to purify IREP in a sample. For example, such antibodies can be attached to a solid substrate such as a resin and can be used to affinity purify the IREP. In addition, the anti-IREP antibody can be used to identify the presence of the IREP in a sample. In this case, the antibody can be labeled with a detectable moiety such as a radioisotope, an enzyme, a fluorochrome or biotin. An anti-IREP antibody can be detectably labeled using methods well known in the art (e.g., Harlow and Lane, supra, (1988) (chapter 9)). Following contact of a labeled anti-IREP antibody with a sample, specifically bound labeled antibody can be identified by detecting the moiety.

The binding of an anti-IREP antibody to the IREP also can be determined using immunological binding reagents. As used herein, an immunological binding reagent includes any type of biomolecule that is useful to detect an antibody molecule. An immunological binding reagent can include a labeled second antibody. A second antibody generally will be specific for the particular class of the first antibody. For example, if an anti-IREP antibody (i.e., a first antibody) is of the IgG class, a second antibody will be an anti-IgG antibody. Such second antibodies are readily available from commercial sources. The second antibody can be labeled using a detectable moiety as described above. When a sample is labeled using a second antibody, the sample is first contacted with a first antibody (i.e., anti-IREP antibody), then the sample is contacted with the labeled second antibody, which specifically binds to the first antibody and results in a labeled sample. Alternatively, a labeled second antibody can be one that reacts with a chemical moiety, for example biotin or a hapten that has been conjugated to the first antibody (e.g., Harlow and Lane, supra, (1988) (chapter 9)). Immunological binding agents also can include avidin or streptavidin when the anti-IREP antibody is labeled with biotin.

Principally, all conventional immunoassays are suitable for the detection of IREPs. Direct binding as discussed above or competitive tests can be used. In a competitive test, the antibody can be incubated with a sample and with the IREP or a fragment thereof (produced as described herein) both simultaneously or sequentially. The IREP from the sample preferably competes with the added IREP (hapten) of the invention for the binding to the antibody, so that the binding of the antibody to the hapten in accordance with the invention is a measure for the quantity of antigen contained in the sample. In a heterogeneous competitive immunoassay where the liquid phase is separated from the solid phase, both the antibody or the peptide can be labeled or bound to a solid phase. The exact amount of antigen contained in the sample can then be determined in a conventional manner by comparison with a standard treated in the same manner.

All competitive test formats that are known to the expert can be used for the detection. The detection can be carried out, for example, using the turbidimetric inhibition immunoassay (TINIA) or a latex particle immunoassay (LPIA). When a TINIA is used, the peptide or peptide derivative of the invention is bound to a carrier such as dextran (EP-A-0 545 350). This polyhapten competes with the analyte contained in the sample for the binding to the antibody. The formed complex can be determined either turbidimetrically or nephelometrically. When an LPIA is employed, particles, preferably latex particles, are coated with the peptides of the invention and mixed with the antibody of the invention and the sample. When an analyte is present in the sample, agglutination is reduced.

Enzyme immunoassays (Wisdom, *Clin. Chem.*, 22(8): 1243–1255 (1976), and Oellerich, *J. Clin. Chem. Clin. Biochem.*, 18:197–208 (1980)), fluorescence polarization immunoassays (FPIA) (Dandliker et al., *J. Exp. Med*, 122:1029 (1965)), enzyme-multiplied immunoassay technology (EMIT) (Rubenstein, *Biochem. Biophys. Res. Comm.*, 47:846–851 (1972)) or the CEDIA technology (Henderson et al., *Clin. Chem.*, 32:1637–41 (1986)) also are suitable immunological based assays for detection of intronic IREPs.

If useful, organisms can be identified using both nucleic acid based detection of an intronic region and the immunological approach which uses anti-IREP antibodies to identify intronic regions encoding a protein.

F. Methods of Identifying an Organism in a Sample

The present invention also provides methods of identifying the presence of a specific organism in a sample, comprising detecting the presence or absence of one or more intronic regions in the nucleic acid of the organism that are characteristic of the organism. The method of detection can be used to diagnose the presence of virtually any organism that contains DNA including fungi, protozoans and other members of the animal kingdom and members of the plant kingdom. Fungi suitable for detection by intron polymorphism analysis include members of the genus of Candida, Aspergillus, Coccidiodes, Cryptococcus, Histoplasma, Blastomyces, Cladosporium for clinical applications, and Aspergillus, Fusarium, Tilletia, Puccinia, Septoria, Botrytis, Pyrenophora, and Gaeumannomyces for nonclinical applications.

An organism can be identified by detecting the presence or absence of one or more intronic regions. The number of intronic regions that need to be evaluated for identifying a particular organism depends on a number of factors, including the uniqueness of a particular intronic region and the potential for related species of organisms to be present in the sample. Generally, a lesser number of introns will need to be evaluated if the goal is to determine a broad classification of the infecting organisms, such as family or genus. In contrast, a larger number of introns generally will need to be analyzed if the goal is to identify a single species of organism or distinguish between races or strains of a single species. By evaluating a sufficient number of intronic regions, the identity of the organism can be established with confidence and significant false negative and false positive results avoided.

In addition, an organism can be identified by detecting intronic regions from more than one source. Thus, intronic regions from different genes can be detected and these genes can be from nuclear DNA or organellar DNA.

Detecting the presence or absence of intronic regions can be accomplished by a variety of methods well known in the art for detecting nucleic acids. These include, for example, primer extension reactions, separation of amplified products by molecular weight, nucleotide sequencing, RFLP or hybridization with a specific nucleic acid probe.

Detection by Primer Extension

The approaches described above for identifying intronic regions that can differentiate between or among taxonomic groups by primer extension also are generally applicable for identifying a specific organism in a sample. For example, the strategy for designing intronic region-specific primers are similar for both identification of intronic regions and for detecting such regions for organism identification. Both first generation and second generation intronic region-specific pairs are useful for organism identification. Second generation primers, however, are preferred because they are complementary and, therefore, can be used in primer extension reactions under high.stringency conditions. Also, PCR is the preferred choice of primer extension reaction.

In one embodiment, the amplifying primer sites are in the exon sequence immediately adjacent to the intron insertion site of the gene. In this case, primer extension will result in a very small sized product (about the combined length of the two primers or so) if the template DNA lacks the intronic region and potentially a much larger product if the template DNA contains the intronic region. In another embodiment, the amplifying primers are located farther from the intron insertion site, for example in a non-flanking exon. In this case, primer extension will generate a larger product than in the case when the primer sites directly flank the intronic region. In yet another embodiment, the intronic region-specific primer sites are located sufficiently far apart so that they span more than one intron insertion site. In this way, amplification by primer extension can generate a product that contains multiple intronic regions.

The intronic region-specific primer sites are preferably located in conservative regions of the gene. In one embodiment, the intronic region-specific primer sites are located in a conserved region of the intron or in an adjacent, upstream and/or downstream exon sequence. In another embodiment, the intronic region-specific primer sites are located in an upstream or downstream intron.

Detection by Probe Hybridization

The presence or absence of a particular intronic region can be determined by standard hybridization with a nucleic acid probe. The probe is preferably a second generation intronic region-specific primer or any other polynucleotide that is complementary to the target sequence. Such probes can be prepared by synthesis or be obtained from nucleic acid vectors containing the probe sequence.

Amplified nucleic acid sequences derived from primer extension with the intronic region-specific primers also can be used as a probe for detecting the presence or absence of an intronic region.

The probe can be labeled with a detectable atom, radical or ligand using any of a variety of known labeling techniques. For example, the probe can be labeled with $^{32}$P by nick translation with an alpha-$^{32}$P-dNTP (Rigby et al., *J. Mol. Biol.*, 113:237 (1977)) or labeled with an enzyme, such as horseradish peroxidase and binding detected by production of a visible substrate. Methods of preparing and labeling probes are well known in the art (e.g., Sambrook et al., supra, (1989) (11.21–11.44)).

Where the nucleic acid containing a target sequence is in a double stranded (ds) form, it is preferred to first denature the dsDNA, as by heating or alkali treatment, prior to conducting the hybridization reaction. The denaturation of the dsDNA can be carried out before or after adding the probe.

The amount of nucleic acid probe used in the hybridization reaction is generally well known and is typically expressed in terms of molar ratios between the probe and the target. Preferred ratios contain equimolar amounts of the target sequence and the probe although it is well known that deviations from equal molarity will produce hybridization reaction products at lower efficiency. Thus, although ratios can be used where one component is included at 1 00-fold molar excess relative to the other component, excesses of less than 50-fold, preferably less than 10-fold, and more preferably less than two-fold are desirable in practicing the invention.

Inclusion of Controls for Detecting Organisms

The present methods of detecting an organism in a sample also can include controls to avoid false negative and false positive results. False-positive results are avoided if the detection method used is highly selective. In primer extension reactions, it is recommended to include internal controls and to confirm any new or unusual results by an independent amplification reaction (Ieven, et al., *Clin. Microbiol. Rev.*, 10:242–256 (1997)). False-positive results also can be prevented by removing sources of contamination in sample handling or carryover from previous experiments.

The detection method disclosed herein avoids many of these difficulties because a collection of intronic region-specific primers is used to yield independent products. For example, an unexpected novel combination of previously known products or a set of previously unknown products would signal a possible false positive that could then be confirmed in an independent DNA sample with other primer pairs.

False-negative results occur when a detection method lacks sensitivity or is subject to a sampling error (e.g., when a PCR is performed on an aliquot that lacks template). When detecting pathogens directly in a sample (e.g., a field or clinical specimen), the lack of sensitivity can be due to the presence of some unknown inhibitor of the primer extension reaction. A polynucleotide whose sequence is derived from the diagnostic primer sequences, along with the diagnostic primers can be used in primer extension to yield an internal control product that is easily distinguished from the expected product by its larger size. The internal control product, when co-amplified with a titration of known amounts of target DNA, also can be used to quantify the amount of template present in the sample (e.g., Honeycutt et al., *Anal. Biochem.*, 248:303–306 (1997)).

The sensitivity of the method to detect an intronic region can be increased with the use of second generation primers. Second generation primers are based on the intronic sequence and exonic flanking sequences determined with first generation primers. Sensitivity can be increased by selecting primer sites for the second generation primers that yield a small product in the PCR when target template is present. The second-generation primers are complementary to the target nucleic acid and, therefore, can be used under conditions of high stringency in the PCR. Under such conditions, the small PCR product can out-compete larger arbitrary PCR products that might arise from the host genome, thus increasing the sensitivity of the detection method. Small products also are amenable to existing automated TAQMAN® (Perkin-Elmer, Foster City, Calif.: Holland et al., *Proc. Natl. Acad. Sci* (USA), 88:7276–7280 (1991) as well as non-PCR amplification technologies such as NASBA, LCR, SDA and TMA.

Detection by Immunological Methods

The identity of a particular organism in a sample can be determined by detecting the presence or absence of particular intronic regions that encode IREPs. Detection of such IREPs, which indirectly indicate the presence of the encoding intronic region, can be accomplished by immunological based assays using anti-IREPs produced as described above. Principally, all conventional immunoassays are suitable for the detection of IREPs including direct binding or competitive tests as discussed above.

G. Kits for Detecting Intronic Regions

The present invention also provides kits that incorporate the components of the invention and makes possible convenient performance of the invention. Kits of the invention comprise one or more of the reagents used in the above described methods and may also include other materials that would make the invention a part of other procedures including adaptation to multi-well technologies. The items comprising the kit may be supplied in separate vials or may be mixed together, where appropriate.

In one embodiment, a kit comprises at least one intron-amplifying-specific primer pair in a suitable container. Preferably the kit contains two or more intronic region-specific primer pairs. In another embodiment, the primer pairs are useful for different intronic regions of different genes and are in separate containers. In another embodiment, the primer pairs are specific for intronic regions of a single gene. Primer pairs can be combined provided there is no interference when used together in amplification or hybridization methods. If necessary, individual primers of each primer pair can be kept in separate vials.

The kit additionally can include in internal amplification control that contains a primer site for the intronic region-specific primers. Additional reagents such as amplification buffer, digestion buffer, a DNA polymerase and nucleoside triphosphates also can be included in the kit.

The primers can be provided in a small volume (e.g., 100 µl) of a suitable solution such as sterile water or Tris buffer and can be frozen. Alternatively, the primers can be air-dried. In another embodiment, a kit comprises, in separate containers, an intronic region-specific probe and solutions for performing hybridization.

In other embodiments, kits are provided for immunological based detection of intronic regions that are expressed by the organism. Such kits can include one or more specific antibody, and an immunological binding reagent to detect binding of the specific antibody. These reagents are preferably provided in separate containers.

EXAMPLES

Example 1

Consensus Alignment of Mitochondrial Gene Homologs

This example shows the selection and alignment of mitochondrial gene homologs of the cytochrome oxidase subunit 1 (cox1) gene for identifying introns suitable for discrimination between species of the fungal genus, Candida. Cox1 gene sequences are available representing a larger number of accessions than other mitochondrial genes and the gene is common to all fungi.

The cox1 sequences of fifteen accessions were downloaded from GOBASE, an Organelle Genome Database (http://megasun.bch.umontreal.ca/gobase/) as individual exon sequence files, and then merged. Of the fifteen accessions, thirteen are Ascomycetes, one is a Basidiomycete, and one is a Chytridiomycete. The cox1 gene of eleven of these accessions is interrupted by at least one intron with the number of introns varying between one and sixteen. The exon sequences were aligned using MAP (Multiple Alignment Program).

The position of intron insertion sites in cox1 was manually located on the exon alignments of the accessions containing introns. FIG. 1 schematically depicts the location of a total of 38 unique intron insertions sites which are distributed along approximately 1400 of the 1800 bases in the exon consensus alignment in the cox1 gene. Primer pairs were derived that flanked four different multiple intron-containing regions as depicted in FIG. 1. The large number of introns in cox 1 provides an abundance of potential "intron amplifying" primer targets.

Example 2

Designing Intronic Region-Specific Primer Pairs

In this example, four multiple intronic region primer pairs were designed that collectively flank a total of 18 of the intron insertion sites in the cox1 gene as depicted in FIG. 1. The primers were derived from the most conserved regions within the gene and contained the majority base of the alignment at each position. The 3'-most base of the primer was situated either in the first or second position within the reading frame so that the 3'-most base was not in wobble position of a codon. The primer was chosen so that there is no redundant base in the 3'-most position of the primer. In this manner, the primers had the greatest utility for testing a wide taxonomic group of accessions. The primers contained 20 to 23 nt with a GC content of 50% and similar predicted melting temperatures.

A total of 28 intronic region region-specific primers were designed based on the Cox1, Cox2 and NadI mitochondrial sequences. Sixteen primers were designed for Cox1 intronic regions (SEQ ID Nos. 1–16), eight primers were designed for Cox2 (SEQ ID Nos. 17–24) and four primers were designed for NadI intronic sequences. The primers are listed in the table below.

TABLE 1

Intronic Region-Specific Primers for Fungal Mitochondrial Introns

| Probe Designation | Nucleotide Sequence (5'–3') |
|---|---|
| cox1B4483 (SEQ ID NO: 1) | GCCTCCCTCATTATTATTATT |
| cox1B4803 (SEQ ID NO: 2) | CATTAGTTGAAAATGGAGCTG |
| cox1B5665 (SEQ ID NO: 3) | AATCTACGGTACCTCCAGAATG |
| cox1B5855 (SEQ ID NO: 4) | CTGTAAACTAAATATAGCTAAAT |
| cox1B8975 (SEQ ID NO: 5) | CTTACTATCCCAAATCCTGGT |
| cox1B7483 (SEQ ID NO: 6) | CATTACAATGTTATTAACTGATAGA |
| cox1B8103 (SEQ ID NO: 7) | GAGATCCTATTTTATATCAAC |
| cox1B9295 (SEQ ID NO: 8) | TAGGTTTACCTGAAAATGTTGA |
| cox1B10173 (SEQ ID NO: 9) | TAGGTTTAGATGTAGATACGAGA |
| cox1B10623 (SEQ ID NO: 10) | TGGTTATAGCTGTTCCAACTG |
| cox1B11255 (SEQ ID NO: 11) | CTACCACCATATAATGTAG |
| cox1B11655 (SEQ ID NO: 12) | ACCTAATACAAATAATAATGGT |
| cox1B11213 (SEQ ID NO: 13) | GGTAGTTTAAGATATAATACAC |
| cox1B11703 (SEQ ID NO: 14) | TGACTTTATTCACTATAGGAG |
| cox1B12225 (SEQ ID NO: 15) | AGAAGCATTAGATAATACTAC |
| cox1B12965 (SEQ ID NO: 16) | TACAGCTCCCATAGATAATACA |
| cox2B5433 (SEQ ID NO: 17) | ACCTACAGGAGTGCATATTCGA |
| cox2B5963 (SEQ ID NO: 18) | ACTTCGCCGTACCATCATTAGG |
| cox2B6805 (SEQ ID NO: 19) | CTTCACGTTTGATTAGTACTGA |
| cox2B7055 (SEQ ID NO: 20) | TCTCAACATTGTCCGTAGAATAC |
| cox2B6573 (SEQ ID NO: 21) | CATCAGTACTAATCAAACGAG |
| cox2B6813 (SEQ ID NO: 22) | GAGTATTCTACGGACAATGT |
| cox2B7545 (SEQ ID NO: 23) | TGATTCTACGGCAATAGGCA |
| cox2B7955 (SEQ ID NO: 24) | GATTGTGAGTCAAGCCAGCTT |
| nad1B9983 (SEQ ID NO: 25) | ATGTTCTGTTTCTTATTCGTATG |
| nad1B10273 (SEQ ID NO: 26) | TGCTACTCTACCTCGACTAC |
| nad1B10725 (SEQ ID NO: 27) | ACAGAAGACCATTAACTGATC |
| nad1B11075 (SEQ ID NO: 28) | ACTAGAGCGATAGCAATAG |

The primers in Table 1 can be used in combinations of a 5'-3' sense strand primer with a 3'-5' anti-sense strand primer.

Primer designation numbers ending in "3" (e.g., cox1B4483), represent sense strand primers for which nucleotide synthesis occurs off the 3' end of the primer. Primer designation numbers ending in "5" (e.g., cox1B5665), represent anti-sense strand primers for which nucleotide synthesis occurs off the 5' end of the primer. Thus, cox1B4483 and cox1B5665 can be used together as primer pairs to amplify a cox1 gene intron. The same applies for the cox2 primers and for the nadI primers. However, not all combinations of 3' and 5' primer pairs will necessarily work in PCR. In some cases, the distance between the 3' and 5' primers is too great for successful amplification.

Example 3

Use of Intronic Region-specific Primer Pairs in PCR With Fungal DNA Templates

Fungi representing 11 genera and 24 species were tested as DNA templates in a PCR using the four intron amplifying primer pairs derived from the cox 1 gene discussed in Example 2. These fungi are phylogenetically distinct and many are of agronomic significance. Fungi found in humans were included as convenient Ascomycete "outgroups."

Courtesy permits for transport of pathogen DNA were obtained from USDA-APHIS (Permit 34327) and from the California Department of Food and Agriculture (Permit #1719). Results were obtained from the following isolates: 3 isolates of *Puccinia graminis*; 1 isolate of *P. coronata* and *P. horiana*; 1 isolate each *Tilletia indica, T. horrida, T. tritici*, and T. species (spp.); 1 isolate of *Lycoperdon pyridome*; 1 isolate each of *Fusarium moniliforme* and *F. graminearum*, 3 isolates of *Aspergillus fumigatus* and 1 isolate each of *A. flavus, A. nidulans*, and *A. niger*; 2 isolates of *Cryptococcus neoformans*; 3 isolates each of *Saccharomyces cerevisiae, Candida albicans, C. glabrata, C. krusei, C. parapsilosis*, and *C. tropicalis*. The strains were recent field isolates obtained as DNA from Dr. Les Szabo, CDL, USDA-ARS, St. Paul, Minn. Additional fungal samples were obtained from Dr. Mary Palm, USDA-APHIS, Mycology Laboratory, Beltsville, Md., Dr. Jon Duvick, Plant Pathologist, Pioneer Hi-Bred International, Johnston, Iowa., and Ms. Pat Nolan, Plant Pathologist, San Diego County Agriculture Commission. Fungal isolates from humans were obtained as DNA from Dr. Brad Cookson, U of WA, Seattle.

PCR reaction conditions for cox1B8103+cox1B8975 primer pairs are as follows: Reaction mix contained 1 U AMPLITAQ® polymerase (Perkin-Elmer), 50 mM KCl, 10 mM Tris-HCl (pH 8.3), 0.1 mM each dNTP (Ultrapure, Amersham-Pharmacia Biotech), 0.5 µM each primer, 50 to 100 ng DNA template. Reaction cocktail was heated to 80° C. for 2 min in GENEAMP® 9600 PCR machine (Perkin-Elmer), then 2.0 mM $MgCl_2$ was added for a total volume of 20 µL. PCR was performed for 35 cycles (94° C., 30 sec denature, 43° C., 30 sec anneal, 72° C., 2 min extension), followed by 6 min extension at 72° C. PCR products were resolved by loading 5.0 µL of the reaction onto a 1% agarose gel (Low EEO, Fisher Scientific) prepared in 1×TBE buffer and subjected to electrophoresis at 10 V $cm^{-1}$, then visualized by ethidium bromide staining.

PCR results using the cox1B8103+cox1B8975 primer pair and the cox1B11703+cox1B12965 primer pair are summarized in Table 1 and Table 2, respectively. Some of the products were cloned and sequenced to confirm their origin from the target exon as indicated.

Based on sequence motifs, all of the amplified introns are Group I introns and all except one contain at least one ORF based on analysis using MacVector v.5.0.2 (Oxford Molecular Group, Oxford, UK). Both homologous and non-homologous introns are amplified using the cox1B8103+cox1B8975 primer pair. Homologous introns from *T. indica, T. tritici*, and *L. pyriforme* are inserted at base 839 (on the cox1 consensus alignment), which is the known site of an intron in *Saccharomyces douglasii* (cox1 intron 2; GenBank accession #M97514) and *Podospora anserina* (cox1 intron 8; GenBank accession #X55026). Introns in *T. horrida* and *C. tropicalis* are inserted at base 850, and are homologous to introns from *S. cerevisiae* (cox1/oxi3 intron 4 GenBank accession #V00694), *P. anserina* (cox1 intron 9; GenBank accession #X55026), and *Pichia canadensis* (cox1 intron 2; GenBank accession #D31785).

In the tables below, *P. horiana* failed to yield a product with the primer pair cox1B8103+cox1B8975 and *C. tropicalis* failed to yield a product with the primer pair cox1B11703+cox1B12965, suggesting that the primers span an intron insertion site unique to *P. horiana* or *C. tropicalis*, respectively. Alternatively, an intron is present in each of these cases, but too large for resolution under the conditions used. Neither the single *P. graminis* or *F. moniliforme* isolate, nor the three isolates of *C. krusei, C. albicans, T. glabrata, A. fumigatus*, and *A. flavus*, or the two isolates of *C. neoformans* contain an intron in the cox1 gene in the region flanked by the cox1B8130 and cox1B8975 primers. The remainder of the isolates tested with these primers have an intron, and with the exception of *T. tritici*, of greater than 900 bp.

TABLE 1

Results of PCR using cox1B8103 + cox1B8975

| Species | Isolate | Product[a] | Intron[b] | Comments[c] |
|---|---|---|---|---|
| *P. graminis* | CRL78 | ~90 bp | | |
| *P. horiana* | 1 | none | | |
| *L. pyriforme* | ATCC46442 | 1547 bp | 1459 bp | blastp:nr $9e^{-19}$ cox1 intron |
| *T. indica* | 1 | 1523 bp | 1435 bp | blastn:nr $4e^{-41}$ cox1 *P. anserina* |
| *T. tritici* | 1 | 372 bp | 291 bp | blastn:nr $3e^{-12}$ cox1 *P. anserina* |
| *T. horrida* | 1 | 1060 bp | 972 bp | blastn:nr $1e^{-138}$ cox1 Peperomia |
| *S. cerevisiae* | AB1380 | ~1000 bp | ~920 bp | expected size for *S. cerevisiae* cox1I4 intron |
| *C. albicans* | 1 | 88 bp | none | |
| *C. albicans* | 2 | 88 bp | none | |
| *C. albicans* | 3 | 88 bp | none | |
| *C. glabrata* | 1 | 88 bp | none | |
| *C. glabrata* | 2 | 88 bp | none | |

TABLE 1-continued

Results of PCR using cox1B8103 + cox1B8975

| Species | Isolate | Product[a] | Intron[b] | Comments[c] |
|---|---|---|---|---|
| C. glabrata | 3 | 88 bp | none | |
| C. krusei | 1 | 88 bp | none | aligns to cox1 exon |
| C. krusei | 2 | 88 bp | none | aligns to cox1 exon |
| C. krusei | 3 | 88 bp | none | aligns to cox1 exon |
| C. tropicalis | 1 | 1055 bp | 968 bp | blastn:nr 6e$^{-07}$ cox1 Marchantia |
| C. tropicalis | 2 | 1055 bp | 968 bp | |
| C. tropicalis | 3 | 1055 bp | 968 bp | |
| C. neoformans | 1 | 88 bp | none | |
| C. neoformans | 2 | 88 bp | none | |
| Fusarium moniliforme | 1 | 88 bp | none | |
| A. flavus | 1 | 88 bp | none | |
| A. flavus | 2 | 88 bp | none | |
| A. flavus | 3 | 88 bp | none | |
| A. fumigatus | 1 | 88 bp | none | |
| A. fumigatus | 2 | 88 bp | none | |
| A. fumigatus | 3 | 88 bp | none | |
| A. niger | 1 | 1481 bp | 1393 bp | blastn:nr 1e$^{-125}$ cox1 P. anserina |

[a]Product of primer pair; if no intron then expect 88 bp exon fragment
[b]Intron size confirmed by cloning and sequencing
[c]Database queries using intron sequence

TABLE 2

Results of PCR using cox1B11703 + cox1B12965

| Species | Isolate | Product[a] | Intron[b] | Comments[c] |
|---|---|---|---|---|
| P. graminis | CRL78 | ~130 bp | | |
| P. graminis | CRL71 | ~130 bp | | |
| P. horiana | 1 | ~350 bp | ~220 | |
| A. nidulans | 1 | 127 bp | none | |
| A. niger | 1 | 127 bp | none | |
| S. cerevisiae | AB1380 | ~1000 bp | | ~870 bp expected size for S. cerevisiae cox1I5 |
| L. pyriforme | 1 | 127 bp | none | |
| C. tropicalis | 1 | none | | |
| C. tropicalis | 2 | none | | |
| C. tropicalis | 3 | none | | |
| P. fumosoroseus | 1 | 127 bp | none | |

[a]Product of primer pair; if no intron then expect 127 bp exon fragment
[b]Intron size confirmed by cloning and sequencing
[c]Database queries using intron sequences Isolates of different species of the same genus appear to have introns of very different and easily distinguishable lengths as exemplified for Tilletia and Candida in Table 1. These "intronic region-specific" primers yielded products in the Puccinia, Tilletia, Aspergillus and Candida species tested, and the products displayed length polymorphisms between species. The existence of optional introns and sequence differences within introns provides an additional level of potential polymorphisms, which may be exploited further.

Example 4

Establishing Taxa-Specific Mitochondrial Intronic Profiles using Fungal Isolates Cereal diseases are caused by a wide range of fungi that includes all the major fungal subclasses. Identification profiles are developed for 43 taxa representing all the major fungal causing cereal diseases. The taxa used in this example represent the many of the prominent cereal pathogens, including many prominent wheat pathogens.

Species level profiles are possible for some of the genera that are represented by more than one species, such as Puccinia, Tilletia, and Fusarium. For specificity and sensitivity of detection at the level of species, one is limited by the number of isolates that can reasonably be sampled, and on the validity of the current pathogen taxonomy. The difficulties encountered in such efforts may persist even though the genomic regions targeted and the technological approach used may be appropriate.

Figure 2:
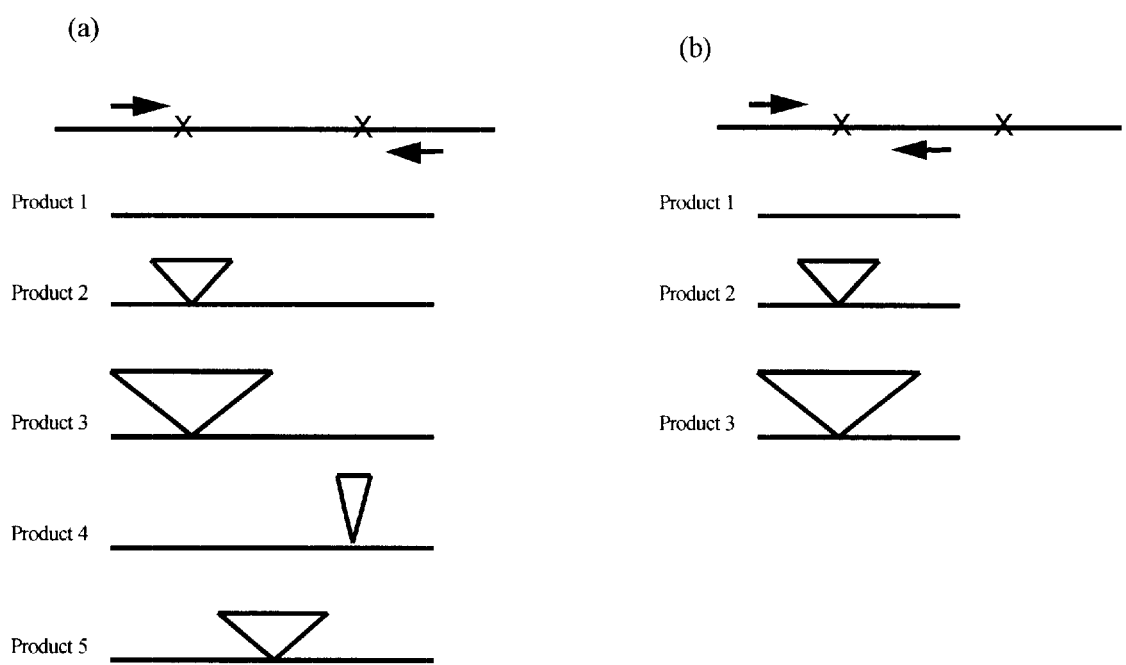
FIGS. 2A and 2B schematically depict potential PCR products using two examples of intronic region-specific primers in a PCR with template DNA that contains two intron insertion sites (labeled as X and Y). The intronic region-specific primers in FIG. 2A are located outside the two intron insertion sites, while in FIG. 2B, the primers are located adjacent only one of the two intron insertions sites (i.e., site X).

DNA is extracted using a modification of Berres et al., Mycologia, 87:821–840 (1995). All reactions are expected to yield a PCR product, even if no intron is found. Only when the intron is too large for PCR or when an accession has multiple introns in a given region will no product be observed with the "intronic-region amplifying" primers (FIG. 2). This instance could result in a false-negative conclusion, so primer pairs that yield no product are omitted from the collection of primer pairs used to generate the identification profile.

PCR is performed and the products are cloned and sequenced (Example 8). The purpose of cloning and sequencing the products of the "first generation" primers is twofold. First, it confirms that the product is derived from the intended target region, and second, it provides sequence information on which to base "second generation" primers that encompass exon sequence variation in cereal pathogens. The sequence information includes the intron and exon-intron boundaries.

Second generation primers are developed that have increased specificity for the given taxa, and that yield small PCR products. The second-generation primers are designed for higher stringency PCR. The small products can outcompete larger, arbitrary PCR products that might arise from the host genome. Small products also are amenable to existing automated TAQMAN® as well as non-PCR amplification technologies such as NASBA, LCR, SDA and TMA.

Some of the first generation primers that are highly specific and yield short products are used for intron profiling of the fungal isolates. Two pairs of primers are chosen that together classify the important species, and, where necessary, a number of other primers are in reserve to use in cases of ambiguity or unexpected results. In this process, primer pairs are identified that distinguish species of some of the genera as well.

The sequence information identifies those introns that encode open reading frames. Monoclonal antibodies are raised against the unique ORFs to detect the intronic polymorphisms in an immunological-based assay.

Example 5

Using Intronic Region-specific Primer Pairs to Identify Organisms in Natural Samples A. Validation using plant specimens:

This example describes how to screen intronic region-specific primer pairs suitable for field sample use by using mock natural samples. Mixtures of extracted fungal DNA and wheat DNA is used as templates in PCR to establish optimum reaction conditions, selectivity, and sensitivity of the primer pairs (i.e., a "mock field" experiment) using intronic region-specific primer pairs for fungal organisms. In the experiment, purified fungal DNA is added to uninfected wheat DNA. DNA also is extracted from actual field specimens of plants suspected of containing fungi. Fungal DNA templates are extracted from infected plant material using the protocol described in Beres et al., supra, (1995).

B. Validation using human specimens:

Mixtures of extracted fungal DNA and human DNA are used to establish optimum reaction conditions, selectivity, and sensitivity of intronic region-specific primer pairs in PCR. Also, in "mock clinical" specimens, extracted fungal DNA is added to uninfected patient serum, blood, or blood cultures. DNA also is extracted from actual clinical specimens known to contain fungi.

Fungal DNA templates are extracted from serum using proteinase K digestion in the presence of Tween 20 (Yamakami et al., *J. Clin. Microbiol.*, 34:2464–24 (1996), and from whole blood using Zymolase with removal of most human DNA after red cell lysis and proteolytic digestion of white blood cells (Einsele et al., *J. Clin. Microbiol.*, 35:1353–1360 (1997), and the addition of benzyl alcohol to remove sodium polyanetholesulfonate (SPS) (Fredricks et al., *J. Clin. Microbiol.*, 36(10):2810–2816 (1998), an inhibitor of PCR. The efficiency can be increased by adding high-speed cellular disruption according to Muller et al., *J. Clin. Microbiol.*, 36(6):1625–1629 (1998), after proteolytic digestion to remove excess sample protein.

Routine blood cultures obtained in the diagnostic laboratory which are positive for microbial growth, and confirmed to contain yeasts by Gram stain examination, are subjected to DNA extraction using the methods disclosed herein and tested in PCR with intronic region-specific primers.

Example 6

Epidemiological Assays for *Puccinia graminis*

This example discloses application of the present methods to identification of the infectious agent in Rust disease of wheat. Rust diseases in wheat involve different parts of the plant and are caused by several members of the genus Puccinia. These species differ in life cycles and levels of genetic diversity. Presently, rust diseases are controlled via corresponding resistance genes bred into commercial wheat varieties. Because cereal rusts have the potential to cause such severe crop loss, they are the subject of annual surveys performed under the auspices of the USDA. The surveys monitor both the titer and distribution of rusts, with particular attention to *P. graminis*, the causal agent of wheat stem rust.

Wheat stem rust is the most aggressive and severe of the wheat rusts and was responsible for dramatic crop losses (up to 70 to 90%) during epidemic outbreaks in the early 1950s (Knott, In: *The Wheat Rusts—Breeding for Resistance*, Springer-Verlag, NY, pp 1–37 (1989)). The durability of the resistance to *P. graminis* in modern wheat varieties has been facilitated by the near-eradication of barberry (*Barberis vulgaris*), the sexual-stage host of *P. graminis*, which has slowed the development of new races of the pathogen. Race designations reflect the status of avirulence and virulence alleles. The intron-targeted strategy described herein is directed to "race"-specific profiles in cases where race designation is fully concordant with genetic clusters defined by molecular approaches.

Homologous introns are amplified and then digested with restriction enzymes to yield sufficient length and restriction enzyme polymorphisms. Also, fragments are resolved on single-stranded conformational polymorphism (SSCP) gels where fragments containing different sequences migrate to different places in the gel, and may be isolated and sequenced if further discrimination is needed. This technique is useful for revealing sequence polymorphisms in tRNA intergenic spacers in bacterial subspecies. PCR products that differed by only 2 out of 70 bases show different mobilities when resolved on a SSCP gel.

Three geographically distinct *P. graminis* f. sp. tritici populations are examined by PCR using primers validated as described above, and template extracted by procedures outlined above. First, members of an asexual clonal population found in the Midwestern U.S. are tested. Eleven races groups are identified in this population based on traditional avirulence/virulence testing with a standard wheat varietal panel, though only nine genetic clusters are confirmed by RAPD fingerprints. Thus, at least three isolates from each of these groups are used. About 25 isolates from a second population found in the Pacific Northwest study and representatives of a third population found in the Northeastern U.S. also are included for completeness.

Example 7

Epidemiological Assays for *A. fumigatus* and *A. flavus*

This example discloses application of the present methods to identification of an infectious human pathogen. Invasive aspergillosis caused by *A. fumigatus* and to a lesser extent by *A. flavus*, is one of the deadliest of fungal infections. An improved diagnostic test to determine the genetic relatedness of clinical and environmental isolates early in the course of an apparent outbreak of invasive aspergillosis should help to identify a specific cause of the outbreak.

Intron specific primers are developed as described above to identify a sufficient combination of common and optional introns such that a profile is established to differentiate individual isolates. If there is insufficient presence or length variability within intronic regions of Aspergillus, sequence variability of homologous introns can be exploited to develop isolate-specific profiles. An initial approach to reveal sequence specific differences is to amplify homologous introns and then digest with restriction enzymes and resolve on single-stranded conformational polymorphism (SSCP) gels. Fragments containing different sequences migrate to different places in the gel and are isolated and sequenced.

Whole blood and serum specimens from human patients are examined for the presence of fungal elements by PCR using intronic region-specific primers and template extracted by procedures disclosed above. The specimens include those obtained for routine laboratory studies of immunocompromised patients who are subsequently diagnosed with invasive aspergillosis by tissue biopsy, or are colonized with Aspergillus, but show no evidence of invasive disease (which serves as controls in these experiments).

Example 8

Confirmed Sequences of Fungal cox1 Mitochondrial Genes

This example discloses six sequences of mitochondrial introns of yeast. Four of the five sequences have open reading frames that could code for a protein (i.e., an IREP), the amino acid sequences of which are disclosed further ahead.

1. Intronic Nucleotide Sequences

A. Cox 1 intron from *Lycoperdon pyriforme*

The sequence of an intron from the cox1 mitochondrial gene was obtained from the organism *Lycoperdon pyriforme* (Strain: ATCC 46442). The sequence is a consensus from 3 clones of a single isolate, each sequenced in both directions. The clones were obtained by cloning amplified DNA using cox1B8103+cox1B8975 primer pairs. The full cloned sequence represents 1547 bp (SEQ ID NO: 29), with the intron at nucleotide position 31–1489 (SEQ ID NO: 30) and with exonic sequence upstream at positions 1–30 (SEQ ID NO: 31) and downstream at position 1490–1547 (SEQ ID NO: 32).

SEQ ID NO: 29 (1–1547)
GAGATCCTATTTTATATCAACACTTATTCT TAA-CAAAAACATTGTACACTATTCCTCTAG-TAGCTAAGAATTCGACAA GCTCCCGCGAGCC-TTTCCAATTTGGCACATTTTTGACACTTTACA-GTAA ACGTTTTCCTAACGCTAAGGCTCCTAGT-CAATCCTTTTTAGATTGGCTA GTGGGATTTTCG-GAAGGAGACGGTAGCTTTATAATCAA-CAGTCGTGGA ACAGCTATTTTCGTGATTACA-CAAAGTACACTTGATCTACAAGTTCTTA AGTATATTCAACGAACTCTAGGTTTTGGTCG-TGTAATTAAACAAGGAC AACGAAC-TAGTCGTTTTGTAGTTGAAGACAACGC-CAGTGTNTGCACTG CTAGTTGCTCTATTTAA-TGGAAATCTAATTTTCACAACTAAACAATCTA GCTTTGCTTTATTTCTTGAAGCCTTTAA-CAAAAGATCATTGTCTTTGGC TACTCAAGCAG-TAGAACTTAAACCGTCACTGATTACTC-CTACTAGACT AAGCATACACGATTTTT-GGTTAGCAGGTTTTACAGACGCTGAAGGTTG CTTCAATTGCTCATTATTAGGTAACTCAAA-CGCGTATAGATTCCGATTT CTTCTAGCA-CAAAAAGGAGAAGTTAATCTAACTGTACTG-ACACAGCTT ACTAAACTTATTGGAGGTGTT-GTTCGTAATCACTCTAAACTGGGAGTA TACGAATTAACTGTCAATGGTGCTCGAAACGT-GGAACGAGTATTCAAA TATTTCGATACTCA-TCCGTTACAAACCAAAAAGCTAATTCG-TACCAA ATATGGCGAGAAGTTCATGCTTC-TATCCTTAAAGGAGAACATCTGTTA CCA-GAGTCTCGAGCAGCACTGAAAGTCAAAGCA-GCTACTATTAATAAC ATGAATTAGTGTACAA-CCCAACGGGAATAAAGGAAGTGGTTCAATGT AATATCTCTTACCTACCAGG CTAACTA-GATTAGAGACAAGTTGTGAAA CTCTAATAG-GCAGGTGTCTATTTTAATTCTAAAGAC-CTGTTAGAGTGA ATAATATTTATACCACTATT-CTAGTCCATATTATACAGGTTGTGTAATC TTTA-GAGAAAAACAGCTTAGCCTTTGTTGCAG-CAGAGCAGCTAATAAT ATGCTTACCCCGACAG-GCGTAAGGATGAACAATTGTTCATTGGCGATA CAAGTGAAAACGGTCAACGTTTGCTC-GAACCAAGACCGTCGGTAGTTT AAACTA-TCGCTACAGACTGGGTCACTTGTGGGT-GCCTGAAAAGGTGCT TAATGTACAGTCGATTC-CTTATATTACACAAGGCTATTGTGCTCTTTAT GAGATTAGGTTTTTAGGTTCCAACAGC-CAAAGCCAGCAGTAGTTTAGG CACTTTCGC-GAGCCTAAATCTACCTGGCCTACTGGGC-TATTAAGCATCC AGCCTACAATAGTA-CATGGGCCCTAGAGAGAGCTAATAAATCTA-GGGT TTTAGGGGATG GGTTTTTTGGTCATCCA-GAAGTTTATATTTTAATTATACCAGGATTTGG GATAGTATG

The insertion site of the intron (SEQ ID NO: 30) is homologous to that of *Saccharomyces douglasii* cox 1 intron 2 (GenBank accession #M97514) and *Podospora anserina* cox 1 intron 8 (GenBank accession #X55026).

B. Cox1 intron from *Tilletia indica*

The sequence of an intron from the cox1 mitochondrial gene was obtained from the organism *Tilletia indica* (Strain: BPI 794197-1, natural isolate from wheat). The sequence is a consensus from 3 clones of a single isolate, each sequenced in both directions. The clones were obtained by cloning amplified DNA using cox1B8103+cox1B8975 primer pairs. The full cloned sequence represents 1523 bp (SEQ ID NO: 33), with the intron at nucleotide position 31–1465 (SEQ ID NO: 34) and with exonic sequence upstream at positions 1–30 (SEQ ID NO: 35) and downstream at position 1466–1523 (SEQ ID NO: 36).

SEQ ID NO: 33 (1–1523)
GAGATCCTATTTTATATCAACACCTATTCT CAC-TACTAAAAGTAGTTATTCTAATTCTATC-TATTTACTTTTTCCAGGTT AAGCTGAATGAG-CCAACCACAAATACTTTTTCCTTTCATAATTTTA-CCC AACAATTTTCATCATTTTATCCT-TCTAAACAAATACCTACTTTTTCTTTC CTAGAATGGCTTGTAGGATTTACTGAAGGAG-ATGGCTGTTTTGTTATG AGCACTCGTGG-TAACTGTATGTTTGTTATTACACAATC-TACTAAGGATA TTCAAGTTCTTCATTTTAT-TCAAGATAAACTAGGATTTGGTCGTGTTAT TAAACAAGGACATTCTACATCTCGTTT-TATTGTTCAGGATAATAAGAA TCTTTATC-TACTTCTACATCTGTTTAATGGTAATCTAGTAC-TT- CCTACTA AAATAGAAAGTTTTAAAAAGTT-TATGGAGATATTTATCAAAAATTCAT CTAATTAT-TCGATTACTCCAATTAGTGTTTGACGAA-CAACACCTAGTTG TAATGACGCTTGAATTA-GCGGATTTACAGATGCTGAAGGATGTTTTAC TTGTTCTCTACTTGGTAATTCTACAGCATAT-CGATTTCGTTTCATGCTTA GTCAAAAAAA-TGAGAAAAATAAGTGTGTACTAGATCATA-TTGCTTTTC TACTAAATGGAAAAGTACGACCT-CACTCTATTCAAGGAGTGTATGAAC TAACTG-TAAACGGAATTTGTAATAATAAAGGAG-TAGTACAATACTTTG ATAAAATATAAACTTTA-CACTAAAAAAGCAAGTTCATATCTACTATGGA AAGAAGTATCAGAGGATCTTAAAGATG-GAAAACATCTTTCTGAAAGTA CTCGTCTAAT-TATGAAAGAAAAGGTAATAAAAATCAAT-AGTTAGAAAT AGTATATAATCTATCCC-ACGGGAATAAAGGGTGTGGTTCTACATAATT TTTATAGTTAATTTAAAATTTTTATATTCCG-ACGCCTTCAGAGCGATTR GAATAAATAAAA-CTAAATTGCCTCTGGGGTCAACGTGTAAA-

AACATAA TAACTATAAAAAAAGAGCGAAATTT-
TATTAGGCAGGTGGTATTTTAAT ATAATGTAAA-
GACCTAATATGATAAAGAGATATTCTC-
TACCACTACTC TAGTCCATGTCGTATAAA-
TCTGTGTAACCTTTAGAGGAAAACAGGTTT
TAAGTATGTTTATGCCCACAGGCATAAA-
GTGATTCTAAAAAATCATCG GCAATACAAGT-
GAAAACGGTCAACGTATATTCGTATGAA-
GACCGTCGG CAGTCTAAACTGTCGCTACA-
GACTGGGTCACTTGTGGGTACCTGAAAT
GGTGCTTAATGTACAGTCGGCTTTCTCTAATG-
GTAAAATCATTACACA AGGTTATTCTCTCT-
ATAAGAGGTCAGAATAGTACAGGGATTT-
CTAAGA GAACTGATAAATTAGAAATTTGG-
GAAAGTG GGTTCTTCGGTCATCCTGAAGTT-
TATATCCTGATTATACCAGGATTTGG GATAG-
TAAG

The insertion site of the intron (SEQ ID NO: 33) is homologous to that of *Saccharomyces douglasii* cox 1 intron 2 (GenBank accession #M97514) and *Podospora anserina* cox 1 intron 8 (GenBank accession #X55026).

C. Cox1 intron from *Tilletia horrida*

The sequence of an intron from the cox1 mitochondrial gene was obtained from the organism *Tilletia horida* (Strain: BPI 802756-1, natural isolate). The sequence is a consensus from 3 clones from a single isolate, each sequenced in both directions. The clones were obtained by cloning amplified DNA using cox1B8103+cox1B8975 primer pairs. The full cloned sequence represents 1060 bp (SEQ ID NO: 37), with the intron at nucleotide position 42–1013 (SEQ ID NO: 38) and with exonic sequence upstream at positions 1–41 (SEQ ID NO: 39) and downstream at position 1014–1060 (SEQ ID NO: 40).

SEQ ID NO: 37 (1–1060)
GAGATCCTATTTTATATCAACATCTTTTTTGGTT-
CTTTGGT CGAATATGGCCCGATATACCTATAT-
TCAGAAGGGTATATATGAATTAC ACTGTAT-
GCTGGAAATATCTGTTTAATGTTATTTC-
TACTATCATCATAA GAAGGTATTATTAC-
GAGCATATCCCGATATAGTAAAAATGAAA-
TAACGA AGATACAATCAGCAGGTAACCAAC-
GACGCTCTATAAGCAGTCTAGTAG GAACCA-
CAGAGACTATACGTGTAACAACTTTTT- CAAC-
CACTTTTGGAC AATGGCTAGCTGGCGTTAT-
TGATGGCGATGGAAGTCTACAACTGAGTA
AACAAGGCTATACAAGTCTTGAAATCAC-
TATGGGACTTGAAGATCTTC CTCTACTTCGT-
TATATTCAAGATAAACTTGGAGGATC-
TATTAAAATGCG AACGGAAGCCAAA-
GCTTATCGATATCGTCTACATAATAAAA-
GAGGTAT GATTACTATGATCAACTACAT-
AAACGGAAATATTCGACATTCATCACG
ACTTACACAACTTCACCGAGTATGTTAACAAC-
TTCATATACCTATCATG GAACCGATTCCAC-
TAACGAATGATAATTACTGGTTTGCAG-
GATTTTTTG ATGCAGAAGGTACTATTACGTT-
TAGTTTCAAGAATGAATATCCTCAAC TAA-
GCATACGAGTATCTAATAAAAACATG-
GAAGACGTTCAGTGGTATA AAAATATA-
TTTGGAGGCTATATCTATTTTGATAGTAGTCAA-
TATGGTCA TTATCAATGGTCAGTGCAAAGACG-
TAATGATGTTATAAGAATGAGAAG ATATTT-
CAAGAATAAATGTAAAAGTCATAAAT-
CAAACCGATTTTTCCT TATATCGGATTATTAT-
CAACTTTCAGATCTAAAAGCATATAAAAAGA
GAGTTAATATAATAATCTGTGGCACTATTTT-
GTCCAAAAGTGGGACAA ATTAAGTTGAAG-
ATAAAGTCCATTTTATTTTACTGTGTAATAT-
AGTAAA AAAAAG CATCCCGAAGTTTATAT-
TCTAATTATACCAGGATTTGGGATAGTAAG

The insertion site of the intron (SEQ ID NO: 37) is homologous to that of *Saccharomyces cerevisiae* cox1/oxi3 intron 4 (GenBank accession #V00694), *Podospora anserina* cox1 intron 9 (GenBank accession #X55026) and *Pichia canadensis* cox1 intron 2 (GenBank accession #D31785).

D. Cox1 intron from *Tilletia tritici*

The sequence of an intron from the cox1 mitochondrial gene was obtained from the organism *Tilletia tritici* (Strain: T-1, natural isolate from wheat). The sequence is a consensus from 3 clones of a single isolate, each sequenced in both directions. The clones were obtained by cloning amplified DNA using cox1B8103+cox1B8975 primer pairs. The full cloned sequence represents 372 bp (SEQ ID NO: 41), with the intron at nucleotide position 31–321 (SEQ ID NO: 42) and with exonic sequence upstream at positions 1–30 (SEQ ID NO: 43) and downstream at position 322–372 (SEQ ID NO: 44).

SEQ ID NO: 41 (1–372)
GAGATCCTATTTTATATCAACACCTGTTCT CAC-
TACTAAGACTAGTTATTCTAATTCTATC-
TATTTATTTTTTCCAGCTT ACGCAGGATCAA-
CAAACCATAAATACCTTTTCCTTTCATAATTTT-
ACTG AACAATTTAAAACCACATCATTTTTC-
CCTTCTAAACAAGTACCTACTTC TTCTTTT-
CTAGAATGGTTTGTAGGATTTACTGAAGGAG-
ACGGCAGTTTT GTTGTAAGCACTCGTGG-
TAACTGTATGTTTGTTATTACACAATCTACTA
AGGATATTCAAGTTCTTCATTTTATCTTTGCTT-
TACGGCTCCGCG ANTTATATATAATAAAAAAGT-
TCAAGATAAACCAGGATTTGGGATAG AAG

The insertion site of the intron (SEQ ID NO: 42) is homologous to that of *Saccharomyces douglasii* cox 1 intron 2 (GenBank accession #M97514) and *Podospora anserina* cox 1 intron 8 (GenBank accession #X55026).

E. Cox1 intron from *Candida tropicalis*

The sequence of an intron from the cox1 mitochondrial gene was obtained from the organism *Candida tropicalis* (isolate from human). The sequence is a consensus from 2 clones each from a separate isolate, each sequenced in both directions. The clones were obtained by cloning amplified DNA using cox1B8103+cox1B8975 primer pairs. The full cloned sequence represents 1055 bp (SEQ ID NO: 45), with the intron at nucleotide position 42–1009 (SEQ ID NO: 46) and with exonic sequence upstream at positions 1–41 (SEQ ID NO: 47) and downstream at position 1010–1055 (SEQ ID NO: 48).

SEQ ID NO: 45 (1–1055)
GAGATCCTATTTTATATCAACACCTCTTCTGA-
TTCTTCGGT CAAGGTTGGCCCTTTGTAATAC-
CCTTATTACATACGCATTACACTATAT GCTG-
GAAACTCCTATGTACATCGTACATAGCT-
TACTTAACTACTCTAGG TATCAGTCTACT-
CCTAGCCCCTAGAGTAAAAAGGTTAA-
GAGATAGTAG CAATACTAGCAGTGATGCAG-
CAGAKAACCAACGGTTCATATTCCAAGC
TATTAATGCCTATGAACTCAGTAGATATTTCAG-
AGACTACACGTGTAA CTGTATCCCCTTCTACG-
GACCCATTCCATCAATGATTAGCTGGTCTAAT
CGATGCTAATGGTGCCTTTAAAATCACT-
CATAAATCACAAGTAAATTG TGAGATAATAGT-
GCCTCAGAACGAGGAAAGAATGTTAA-
GAGTTATTCA AGACAAGTATGGTGGTT-
CTATCAGGCTTAGATCAGGTGATCGTACCCT

TCGTTACAGATTACAAGATAAAGCTAGT-
GTAATCACCTTAATACAACA TGTTAATGG-
TAACCTTCATACTCCTTTAAGATTAAGC-
AACTACATCGG GTATGTCCTCTACTT-
AATATAGAGGCTAACATGCCTATACCTT-
TAACCA TATTTAATGGTTGATTTATGGGC-
TATTTTGATGGTAAAGGTAACATCAG ATGT-
AGAGTACCTAATATCTACTTAAGTGCTACAGGT-
AAAGCTGCAGT AAGTCTTCAAGGTTTTGT-
TGATGTTTTTGGTGGTGAGATAGTATACCGT
AGAGCCAGCHATGGTTCATATACATG-
GAAACTATCCCGTCGACCTAGT GTGCTGTT-
ATTTATGAGGTATCAGAMATGACATATATCACA-
GTCAACA MMGCAGCGGAGATTGGGCTTAAT-
GAGAAAGTCTATCACTTAATTTAC ATGGA-
GAAAAGTGGGGATTTAAAARGATTTTCTCT-
GTTAAAGACATGA GTWTTATTCCATAATAAAT-
GAAAATAAATGCAGAAGATATAGTCCATA CG
CATCCTGAGGKTTATATCCTGATTATAC-
CAGGATTTGGGATAGTWAG

The insertion site of the intron (SEQ ID NO: 46) is homologous to that of *Saccharomyces cerevisiae* cox1/oxi3 intron 4 (GenBank accession #V00694), *Podospora anserina* cox1 intron 9 (GenBank accession #X55026) and *Pichia canadensis* cox1 intron 2 (GenBank accession #D31785).

F. Cox 1 intron from *Aspergillus niger*

The sequence of an intron from the cox1 mitochondrial gene was obtained from the organism *Aspergillus niger* (isolate from human). The sequence is from 2 clones of a single isolate, each sequenced in both directions. The clones were obtained by cloning amplified DNA using cox1B8103+ cox1B8975 primer pairs. The full cloned sequence represents 1481 bp (SEQ ID NO: 55), with the intron at nucleotide position 31–1423 (SEQ ID NO: 56) and with exonic sequence upstream at positions 1–30 (SEQ ID NO: 57) and downstream at position 1424–1481 (SEQ ID NO: 58).

SEQ ID NO: 55 (1–1481)
GAGATCCTATTTTATATCAACATCTTTTCT CAA-
GAGATATTTTAATTAATTGTTTAATAT-
TAACAATTCTAGCTTCAAT AGTAAAGATTAA-
TAAATCAAATTTAAGTTTTAAATTTAATTA-
TAGTACT TTCATAAATAAATTTRATTTTT-
CAAATTTTTATATAAAATTTTCTAATTA TTTAC-
CTAATAATACTTTACCTTCAGAAAAAT-
TCTTGACTTGATTTATA GGATTCACAGAAGGT-
GAGGGGTCATTTATAGTAAATAATAGAGGTGAT
CTTTGTTTTGTTATTACACAAAAAAC-
TATAGATATTGAAATATTAGAAT TTATAAAA-
GAAACTTTAGGTTTTGGTAAAGTAAT-
TCAACAATCTAAAT TAACTAGTAGATAT-
GTTACACAAAACAAAAAAGAAATAGAAA-
TACTT ATTCATTTGTTTAATGGTAATCTTATAT-
TACCAAGTAGAAAGATAAAAT TTGAAAA-
TTTCATTAAAGGATTTAATATTTGAAT-
AGGTAAAGGTAGAA TAAAATTAGATCCTGT-
TGAATTAAAACATAATTTTATTTTACCTAGTTT
AAATAATAGTTGATTGGCAGGTTTTACT-
GATGGGAAGGCTGTYTTAC TTGTTCTATAGG-
TAAAGACAAAGGATTTAGTTTTAATTT-
TAATATTGCT CAAAAATGAGAGGAAAA-
TATTGAAGTATTACAACATCTTTGTACTTTA
TTTAATGGAGGAATAGTCTCAAAACAT-
AGTGTGGATAATGTAAATGAA TTTAGAA-
TAGGAGGATTAAAAAATTGTAAAAATATATTT-
CCCTATTTT GATACTTATACATTATTAAC-
TAAAAAATCTACTAGTTATATTTATGAA
AAGAAATATATGAAGATTTGTTAAAAAAATAT-
CATTTAGACCCAATTA AAAGGGTAGAGATGAT-
TGAAAAAGCTAGATTGATAAATAAAATTAAT
TAATTAAAATATTAGGGAAAAAAAGTAAA-
GGTTTAACGTGCAAGTTTT GAAGCTCTTA-
GGACAGATGTAAAAGGATATAAGATCCAAAA-
GAGCAA ATATTCTATAATGAATATACCTTATACT-
TAGTTAATGTTTAGTTATTAC TACTTGCAAC-
TCTTAAGTGTAACGTATATATAATTTGG-
TATATATTGTT ATACTTATCAATTAATATATAAT-
TGATAAAAGGAAAAGTTAGTATAAA CATTA-
GCGATACTAGTGTTAACGGTCAATAAATTTT-
CATGTTTAAAGA CCGTCGGTTATTTAAGTGAC-
CGCTACAGACTGGTTCACTGGTAGGTGG
CTGAAATGCTGCTTAATGTACAGTCGGT-
TCCTTCCATATTTTATATATG CACAAGCCCA-
GAATTATATAATTACTGGTACCTGGATT-
TAATAAATGA ACATCAATATATTGATGAGAAG-
TTAAATTTGAAGGAATG GATTCTTCGGACATC-
CGGAAGTTTACATCTTAATTATACCAG-
GATTTGG GATAGTAAG

The insertion site of the intron (SEQ ID NO: 56) is homologous to that of *Saccharomyces douglasii* cox 1 intron 2 (GenBank accession #M97514) and *Podospora anserina* cox 1 intron 8 (GenBank accession #X55026).

2. Intronic Open Reading Frame Sequences

MacVector v. 5.0.2 was used for open reading frame (ORF) analysis of the intronic sequences. Search options were set for all possible start/start codons using the yeast mitochondrial genetic code and a minimum of 100 amino acids. The amino acid sequence can vary depending upon the genetic code used for translation. In addition, the intronic sequences and adjacent upstream and downstream exons sequences were analyzed using the same search options to identify potential readthrough, or continuous ORFs. None were found. The intronic sequence ORFs are described below:

A. Cox1 intron from *Candida tropicalis*

One ORF was identified and located from base 202 to 903 in the first frame of the plus strand shown as SEQ ID NO: 45, and is translated below using the yeast mitochondrial genetic code.

SEQ ID NO: 49 (CtropFrame1+/202–903 of SEQ ID NO: 45)

MQQXTNGSYSKTLMPMNSVDISETTRVTVSPST-
DPFHQWLAGTIDANGAF KITHKSQVNCEMM-
VPQNEERMLRVIQDKYGGSIRTRSGDRTTRYR-
LQDK ASVITLMQHVNGNTHTPLRLSQTHRV-
CPTTNMEANMPMPLTMFNGWFM GYFD-
GKGNIRCRVPNIYLSATGKAAVSTQGFVD-
VFGGEMVYRRASXGSY TWKTSRRPSVTLFM-
RYQXWHMSQSTXQRRLGLMRKSIT

B. Cox1 intron from *Tilletia horrida*

Two ORFs were identified in the cloned intronic region shown as SEQ ID NO: 37 (i.e., the plus strand). ORF1 is located from base 81–548 in the third frame (SEQ ID NO: 50) while ORF2 is located from base 570–914 in the third frame (SEQ ID NO:51). Each of the ORFs are translated below using the yeast mitochondrial genetic code.

SEQ ID NO: 50 (ThFrame3+/81–548 of SEQ ID NO: 37)
MNYTVCWKYTFNVISTIIMRGIITSMSRYSKNEM-TKMQSAGNQRRSMSST VGTTETMRVTTFSTTF-GQWTAGVIDGDGSTQTSKQGYTSTEIT-MGTEDTP TTRYIQDKTGGSIKMRTEAKAYRY-RTHNKRGMITMINYMNGNIRHSSRTT QTHRVC SEQ ID NO: 51 (ThFrame3+/570–914 of SEQ ID NO: 37)
MEPIPTTNDNYWFAGFFDAEGTITFSFKNEYPQTS-MRVSNKNMEDVQWY KNMFGGYIY-FDSSQYGHYQWSVQRRNDVMRMRRY-FKNKCKSHKSNRFF TMSDYYQTSDTKAYKKES C. Cox1 intron from *Lycoperdon pyriforme*

One ORF was identified in the minus strand of the intronic region shown as SEQ ID NO: 29. For reference, SEQ ID NO: 52 is the complement of SEQ ID NO: 29 (i.e. the minus strand), shown in a 5'-3' direction and numbered from 1–1547 (i.e., a reverse complement sequence). The ORF (SEQ ID NO: 53) is located from base 646–1254 of SEQ ID NO: 52. The ORF is translated below using the yeast mitochondrial genetic code.

SEQ ID NO: 53 (LpyFrame1–/646–1254 of SEQ ID NO: 52)
MLLMVAALTFSAARDSGNRCSPLRMEAW-TSRHIWYELAFLVCNGWVSK YLNTRSTFRA-PLTVNSYTPSLEWLRTTPPMSLVSCVSTV-RLTSPFCARRNR NTYAFELPNNEQLKQPSASVK-PANQKSCMTSTVGVISDGLSSTAWVAKD NDTLLKASRNKAKTDCLVVKIRFPLNRAT-SSAXTGVVFNYKTTSSLSLFN YTTKT D. Cox1 intron from *Tilletia indica*

One ORF was identified, and located from base 225 to 899 in the third frame of the plus strand, shown as SEQ ID NO: 33, and is translated below using the yeast mitochondrial genetic code.

SEQ ID NO: 54 (TiFrame3+/225–899 of SEQ ID NO: 33)
MSTRGNCMFVITQSTKDIQVTHFIQDKT-GFGRVIKQGHSTSRFIVQDNKNT YTTTHTFNG-NTVTPTKMESFKKFMEMFIKNSSNYSITPIS-VWRTTPSCNDA WISGFTDAEGCFTCSTTGN-STAYRFRFMTSQKNEKNKCVTDHIAFTTNGK VRPHSIQGVYETTVNGICNNKGVVQYFD-KYKTYTKKASSYTTWKEVSED TKDGKHT-SESTRTIMKEKVMKINS E. Cox1 intron from *Tilletia tritici*

No ORFs were identified in the *Tilletia tritici* intron sequence. Analysis of this intron was repeated using a minimum of 50 amino acid search option; no ORFs were identified.

F. Cox 1 intron from *Aspergillus flavus*

One ORF was identified, and located in from base 3 to 950 in the third frame of the plus strand, shown as SEQ ID NO: 55, and is translated below using the mold mitochondrial genetic code.

SEQ ID NO: 59 (AnFrame3+/3–950 of SEQ ID NO: 55)
DPILYQHLFSRDILINCLILTILASIVKINKSNLSFKF-NYSTFINKFXFSNFYIK FSNYLPNNTLPSEKFLT-WFIGFTEGEGSFIVNNRGDLCFVITQK-TIDIEILEFI KETLGFGKVIQQSKLTSRYV-TQNKKEIEILIHLFNGNLILPSRKIKFENFIKG FNI-WIGKGRIKLDPVELKHNFILPSLNNSW-LAGFTDGEGCXTCSIGKDKGF SFNFNIA-QKWEENIEVLQHLCTLFNGGIVSKHSVDNVNE-FRIGGLKNCKNI FPYFDTYTLLTKKSTSYIL-WKEIYEDLLKKYHLDPIKRVEMIEKARLINKIN The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of constructing a profile of intronic region characteristics from a given taxonomic group of organisms, said profile being useful for differentiating between or among selected taxonomic groupings of organisms, comprising the steps of:
   (a) selecting a given taxonomic group of organisms comprising members belonging to smaller taxonomic groups than the given taxonomic group;
   (b) selecting at least one intronic region known to be found in some or all members of the taxonomic group, wherein said intronic region comprises an organellar intron gene sequence or a nuclear Group I or Group II intron gene sequence;
   (c) designing a first set of primers that are complementary to a concensus sequence in the intronic region;
   (d) using the first set of primers to amplify the intronic region from a panel of at least one known member from each of the smaller taxonomic groups thereby forming an amplified nucleic acid product;
   (e) analyzing the amplified nucleic acid product from step (d) to determine characteristics of the intronic region, wherein said characteristics include the presence or absence of an intron gene sequence, the length of the amplified nucleic acid product, the insertion site of the intron gene sequence, and the sequence of the amplified nucleic acid product;
   (f) optionally repeating steps (c) and (d) with a second set of primers, at least one of which has increased specificity for some members of the taxonomic group, and analyzing the amplified nucleic acid product obtained therefrom to determine the length of the amplified nucleic acid product; and
   (g) constructing a profile of the intronic region characteristics, wherein said profile is adapted to differentiate between members of the smaller taxonomic groups within the given taxonomic group.

2. The method of claim 1, wherein the given taxonomic group is a class or subclass of organisms, and wherein the smaller taxonomic groups are genera.

3. The method of claim 1, further comprising the step of hybridizing the amplified products with specific nucleic acid probes.

4. The method of claim 1, wherein the first set of primers flank more than one intron insertion site.

5. The method of claim 1, wherein the first set of primers flank a single intron insertion site.

6. The method of claim 1, wherein the members of the given taxonomic group of organisms are eukaryotes.

7. The method of claim 6, wherein the eukaryotes are fungi.

8. The method of claim 7, wherein the fungi are of the genus Candida or Aspergillus.

9. The method of claim 1, wherein at least one of the primers in the first set of primers is complementary to a sequence of nucleotides in an exon.

10. The method of claim 1, wherein at least one of the primers in the second set of primers is complementary to a sequence of nucleotides in an intron.

11. The method of claim 1, wherein the intronic region further comprises all or a portion of an open reading frame that encodes a protein.

* * * * *

SEQUENCE LISTING

```
<160> NUMBER OF SEQ ID NOS: 59

<210> SEQ ID NO 1
<211> LENGTH: 21
<212> TYPE: DNA
<213> ORGANISM: Artificial Sequence
<220> FEATURE:
<223> OTHER INFORMATION: Primer

<400> SEQUENCE: 1
gcctccctca ttattattat t                                            21

<210> SEQ ID NO 2
<211> LENGTH: 21
<212> TYPE: DNA
<213> ORGANISM: Artificial Sequence
<220> FEATURE:
<223> OTHER INFORMATION: Primer

<400> SEQUENCE: 2
cattagttga aaatggagct g                                            21
```

<210> SEQ ID NO 3
<211> LENGTH: 22
<212> TYPE: DNA
<213> ORGANISM: Artificial Sequence
<220> FEATURE:
<223> OTHER INFORMATION: Primer

<400> SEQUENCE: 3
aatctacggt acctccagaa tg                                              22

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
ctgtaaacta aatatagcta aat                                             23

<210> SEQ ID NO 5
<211> LENGTH: 21
<212> TYPE: DNA
<213> ORGANISM: Artificial Sequence
<220> FEATURE:
<223> OTHER INFORMATION: Primer

<400> SEQUENCE: 5
cttactatcc caaatcctgg t                                               21

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cattacaatg ttattaactg ataga                                           25

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gagatcctat tttatatcaa c                                               21

<210> SEQ ID NO 8
<211> LENGTH: 22
<212> TYPE: DNA
<213> ORGANISM: Artificial Sequence
<220> FEATURE:
<223> OTHER INFORMATION: Primer

<400> SEQUENCE: 8
taggtttacc tgaaatgtt ga                                               22

<210> SEQ ID NO 9
<211> LENGTH: 23
<212> TYPE: DNA
<213> ORGANISM: Artificial Sequence
<220> FEATURE:

-continued

<223> OTHER INFORMATION: Primer

<400> SEQUENCE: 9
taggtttaga tgtagatacg aga                                    23

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
tggttatagc tgttccaact g                                      21

<210> SEQ ID NO 11
<211> LENGTH: 19
<212> TYPE: DNA
<213> ORGANISM: Artificial Sequence
<220> FEATURE:
<223> OTHER INFORMATION: Primer

<400> SEQUENCE: 11
ctaccaccat ataatgtag                                         19

<210> SEQ ID NO 12
<211> LENGTH: 22
<212> TYPE: DNA
<213> ORGANISM: Artificial Sequence
<220> FEATURE:
<223> OTHER INFORMATION: Primer

<400> SEQUENCE: 12
acctaataca aataataatg gt                                     22

<210> SEQ ID NO 13
<211> LENGTH: 22
<212> TYPE: DNA
<213> ORGANISM: Artificial Sequence
<220> FEATURE:
<223> OTHER INFORMATION: Primer

<400> SEQUENCE: 13
ggtagtttaa gatataatac ac                                     22

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
tgactttatt cactatagga g                                      21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
agaagcatta gataatacta c                                      21

```
<210> SEQ ID NO 16
<211> LENGTH: 22
<212> TYPE: DNA
<213> ORGANISM: Artificial Sequence
<220> FEATURE:
<223> OTHER INFORMATION: Primer

<400> SEQUENCE: 16
tacagctccc atagataata ca                                          22

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
acctacagga gtgcatattc ga                                          22

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
acttcgccgt accatcatta gg                                          22

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
cttcacgttt gattagtact ga                                          22

<210> SEQ ID NO 20
<211> LENGTH: 23
<212> TYPE: DNA
<213> ORGANISM: Artificial Sequence
<220> FEATURE:
<223> OTHER INFORMATION: Primer

<400> SEQUENCE: 20
tctcaacatt gtccgtagaa tac                                         23

<210> SEQ ID NO 21
<211> LENGTH: 21
<212> TYPE: DNA
<213> ORGANISM: Artificial Sequence
<220> FEATURE:
<223> OTHER INFORMATION: Primer

<400> SEQUENCE: 21
catcagtact aatcaaacga g                                           21

<210> SEQ ID NO 22
<211> LENGTH: 20
<212> TYPE: DNA
<213> ORGANISM: Artificial Sequence
<220> FEATURE:
<223> OTHER INFORMATION: Primer
```

-continued

```
<210> SEQ ID NO 22
```

<400> SEQUENCE: 22
gagtattcta cggacaatgt                                            20

```
<210> SEQ ID NO 23
<211> LENGTH: 20
<212> TYPE: DNA
<213> ORGANISM: Artificial Sequence
<220> FEATURE:
<223> OTHER INFORMATION: Primer
```

<400> SEQUENCE: 23
tgattctacg gcaataggca                                            20

```
<210> SEQ ID NO 24
<211> LENGTH: 21
<212> TYPE: DNA
<213> ORGANISM: Artificial Sequence
<220> FEATURE:
<223> OTHER INFORMATION: Primer
```

<400> SEQUENCE: 24
gattgtgagt caagccagct t                                          21

```
<210> SEQ ID NO 25
<211> LENGTH: 23
<212> TYPE: DNA
<213> ORGANISM: Artificial Sequence
<220> FEATURE:
<223> OTHER INFORMATION: Primer
```

<400> SEQUENCE: 25
atgttctgtt tcttattcgt atg                                        23

```
<210> SEQ ID NO 26
<211> LENGTH: 20
<212> TYPE: DNA
<213> ORGANISM: Artificial Sequence
<220> FEATURE:
<223> OTHER INFORMATION: Primer
```

<400> SEQUENCE: 26
tgctactcta cctcgactac                                            20

```
<210> SEQ ID NO 27
<211> LENGTH: 21
<212> TYPE: DNA
<213> ORGANISM: Artificial Sequence
<220> FEATURE:
<223> OTHER INFORMATION: Primer
```

<400> SEQUENCE: 27
acagaagacc attaactgat c                                          21

```
<210> SEQ ID NO 28
<211> LENGTH: 19
<212> TYPE: DNA
<213> ORGANISM: Artificial Sequence
<220> FEATURE:
<223> OTHER INFORMATION: Primer
```

<400> SEQUENCE: 28
actagagcga tagcaatag                                             19

```
<210> SEQ ID NO 29
<211> LENGTH: 1547
```

<212> TYPE: DNA
<213> ORGANISM: Lycoperdon pyriforme
<220> FEATURE:
<221> NAME/KEY: misc_feature
<222> LOCATION: (1)...(1547)
<223> OTHER INFORMATION: n = A,T,C or G

<400> SEQUENCE: 29

```
gagatcctat tttatatcaa cacttattct taacaaaaac attgtacact attcctctag      60
tagctaagaa ttcgacaagc tcccgcgagc ctttccaatt tggcacattt ttgacacttt     120
acagtaaacg ttttcctaac gctaaggctc ctagtcaatc cttttagat tggctagtgg      180
gatttcgga aggagacggt agctttataa tcaacagtcg tggaacagct attttcgtga      240
ttacacaaag tacacttgat ctacaagttc ttaagtatat tcaacgaact ctaggttttg     300
gtcgtgtaat taaacaagga caacgaacta gtcgttttgt agttgaagac aacgccagtg     360
tntgcactgc tagttgctct atttaatgga aatctaattt tcacaactaa acaatctagc     420
tttgctttat ttcttgaagc ctttaacaaa agatcattgt ctttggctac tcaagcagta     480
gaacttaaac cgtcactgat tactcctact agactaagca tacacgattt ttggttagca     540
ggttttacag acgctgaagg ttgcttcaat tgctcattat taggtaactc aaacgcgtat     600
agattccgat ttcttctagc acaaaaagga gaagttaatc taactgtact gacacagctt     660
actaaactta ttggaggtgt tgttcgtaat cactctaaac tgggagtata cgaattaact     720
gtcaatggtg ctcgaaacgt ggaacgagta ttcaaatatt tcgatactca tccgttacaa     780
accaaaaaag ctaattcgta ccaaatatgg cgagaagttc atgcttctat ccttaaagga     840
gaacatctgt taccagagtc tcgagcagca ctgaaagtca aagcagctac tattaataac     900
atgaattagt gtacaaccca acgggaataa aggaagtggt tcaatgtaat atctcttacc     960
taccaggcta actagattag agacaagttg tgaaactcta ataggcaggt gtctatttta    1020
attctaaaga cctgttagag tgaataatat ttataccact attctagtcc atattataca    1080
ggttgtgtaa tctttagaga aaaacagctt agcctttgtt gcagcagagc agctaataat    1140
atgcttaccc cgacaggcgt aaggatgaac aattgttcat tggcgataca agtgaaaacg    1200
gtcaacgttt gctcgaacca agaccgtcgg tagtttaaac tatcgctaca gactgggtca    1260
cttgtgggtg cctgaaaagg tgcttaatgt acagtcgatt ccttatatta cacaaggcta    1320
ttgtgctctt tatgagatta ggtttttagg ttccaacagc caaagccagc agtagtttag    1380
gcactttcgc gagcctaaat ctacctggcc tactgggcta ttaagcatcc agcctacaat    1440
agtacatggg ccctagagag agctaataaa tctagggttt tagggatgg gttttttggt    1500
catccagaag tttatatttt aattatacca ggatttggga tagtatg                  1547
```

<210> SEQ ID NO 30
<211> LENGTH: 1459
<212> TYPE: DNA
<213> ORGANISM: Lycoperdon pyriforme
<220> FEATURE:
<221> NAME/KEY: misc_feature
<222> LOCATION: (1)...(1459)
<223> OTHER INFORMATION: n = A,T,C or G

<400> SEQUENCE: 30

```
taacaaaaac attgtacact attcctctag tagctaagaa ttcgacaagc tcccgcgagc      60
ctttccaatt tggcacattt ttgacacttt acagtaaacg ttttcctaac gctaaggctc     120
ctagtcaatc cttttagat tggctagtgg gatttcgga aggagacggt agctttataa       180
```

```
tcaacagtcg tggaacagct attttcgtga ttacacaaag tacacttgat ctacaagttc      240
ttaagtatat tcaacgaact ctaggttttg gtcgtgtaat taaacaagga caacgaacta      300
gtcgttttgt agttgaagac aacgccagtg tntgcactgc tagttgctct atttaatgga      360
aatctaattt tcacaactaa acaatctagc tttgctttat tcttgaagc ctttaacaaa       420 agatcattgt ctttggctac tcaagcagta gaacttaaac cgtcactgat tactcctact      480
agactaagca tacacgattt tggttagca ggttttacag acgctgaagg ttgcttcaat       540
tgctcattat taggtaactc aaacgcgtat agattccgat tcttctagc acaaaaagga      600 gaagttaatc taactgtact gacacagctt actaaactta ttggaggtgt tgttcgtaat      660
cactctaaac tgggagtata cgaattaact gtcaatggtg ctcgaaacgt ggaacgagta     720
ttcaaatatt tcgatactca tccgttacaa accaaaaaag ctaattcgta ccaaatatgg     780
cgagaagttc atgcttctat ccttaaagga gaacatctgt taccagagtc tcgagcagca     840
ctgaaagtca aagcagctac tattaataac atgaattagt gtacaaccca acgggaataa     900
aggaagtggt tcaatgtaat atctcttacc taccaggcta actagattag agacaagttg      960
tgaaactcta ataggcaggt gtctatttta attctaaaga cctgttagag tgaataatat     1020
ttataccact attctagtcc atattataca ggttgtgtaa tctttagaga aaaacagctt     1080
agcctttgtt gcagcagagc agctaataat atgcttaccc cgacaggcgt aaggatgaac     1140
aattgttcat tggcgataca agtgaaaacg gtcaacgttt gctcgaacca agaccgtcgg     1200
tagtttaaac tatcgctaca gactgggtca cttgtgggtg cctgaaaagg tgcttaatgt     1260
acagtcgatt ccttatatta cacaaggcta ttgtgctctt tatgagatta ggttttttagg    1320 ttccaacagc caaagccagc agtagtttag gcactttcgc gagcctaaat ctacctggcc     1380
tactgggcta ttaagcatcc agcctacaat agtacatggg ccctagagag agctaataaa     1440
tctagggttt tagggggatg                                                 1459

<210> SEQ ID NO 31
<211> LENGTH: 30
<212> TYPE: DNA
<213> ORGANISM: Lycoperdon pyriforme

<400> SEQUENCE: 31
gagatcctat tttatatcaa cacttattct                                      30

<210> SEQ ID NO 32
<211> LENGTH: 58
<212> TYPE: DNA
<213> ORGANISM: Lycoperdon pyriforme

<400> SEQUENCE: 32
ggttttttgg tcatccagaa gtttatattt taattatacc aggatttggg atagtatg       58

<210> SEQ ID NO 33
<211> LENGTH: 1523
<212> TYPE: DNA
<213> ORGANISM: Tilletia indica

<400> SEQUENCE: 33
gagatcctat tttatatcaa cacctattct cactactaaa agtagttatt ctaattctat      60
ctatttactt tttccaggtt aagctgaatg agccaaccac aaatactttt tcctttcata     120 attttacccca acaattttca tcattttatc cttctaaaca aatacctact ttttctttcc     180
tagaatggct tgtaggattt actgaaggag atggctgttt tgttatgagc actcgtggta     240
```

```
actgtatgtt tgttattaca caatctacta aggatattca agttcttcat tttattcaag      300
ataaactagg atttggtcgt gttattaaac aaggacattc tacatctcgt tttattgttc      360
aggataataa gaatctttat ctacttctac atctgtttaa tggtaatcta gtacttccta      420
ctaaaataga aagttttaaa agtttatgg agatatttat caaaaattca tctaattatt       480
cgattactcc aattagtgtt tgacgaacaa cacctagttg taatgacgct tgaattagcg      540
gatttacaga tgctgaagga tgttttactt gttctctact tggtaattct acagcatatc      600
gatttcgttt catgcttagt caaaaaaatg agaaaaataa gtgtgtacta gatcatattg      660
cttttctact aaatggaaaa gtacgacctc actctattca aggagtgtat gaactaactg      720
taaacggaat ttgtaataat aaaggagtag tacaatactt tgataaatat aaactttaca      780
ctaaaaaagc aagttcatat ctactatgga agaagtatc agaggatctt aaagatggaa       840
aacatctttc tgaaagtact cgtctaatta tgaaagaaaa ggtaataaaa atcaatagtt      900
agaaatagta tataatctat cccacgggaa taaagggtgt ggttctacat aatttttata     960 gttaattttaa aatttttata ttccgacgcc ttcagagcga ttrgaataaa taaaactaaa    1020
ttgcctctgg ggtcaacgtg taaaaacata ataactataa aaaagagcg aaatttatt      1080 aggcaggtgg tattttaata taatgtaaag acctaatatg ataaagagat attctctacc     1140
actactctag tccatgtcgt ataaatctgt gtaaccttta gaggaaaaca ggttttaagt    1200
atgtttatgc ccacaggcat aaagtgattc taaaaaatca tcggcaatac aagtgaaaac    1260
ggtcaacgta tattcgtatg aagaccgtcg gcagtctaaa ctgtcgctac agactgggtc    1320
acttgtgggt acctgaaatg gtgcttaatg tacagtcggc tttctctaat ggtaaaatca    1380
ttacacaagg ttattctctc tataagaggt cagaatagta cagggatttc taagagaact    1440
gataaattag aaatttggga agtgggttc ttcggtcatc ctgaagttta tatcctgatt     1500
ataccaggat ttgggatagt aag                                              1523

<210> SEQ ID NO 34
<211> LENGTH: 1435
<212> TYPE: DNA
<213> ORGANISM: Tilletia indica

<400> SEQUENCE: 34
cactactaaa agtagttatt ctaattctat ctatttactt tttccaggtt aagctgaatg      60
agccaaccac aaatacttt tcctttcata attttaccca acaattttca tcatttatc       120 cttctaaaca aataccttct ttttcttcc taggatggct tgtaggattt actgaaggag      180
atggctgttt tgttatgagc actcgtggta actgtatgtt tgttattaca caatctacta     240
aggatattca agttcttcat tttattcaag ataaactagg atttggtcgt gttattaaac     300
aaggacattc tacatctcgt tttattgttc aggataataa gaatctttat ctacttctac     360
atctgtttaa tggtaatcta gtacttccta ctaaaataga agttttaaa agtttatgg      420 agatatttat caaaaattca tctaattatt cgattactcc aattagtgtt tgacgaacaa    480
cacctagttg taatgacgct tgaattagcg gatttacaga tgctgaagga tgttttactt    540
gttctctact tggtaattct acagcatatc gatttcgttt catgcttagt caaaaaaatg    600
agaaaaataa gtgtgtacta gatcatattg cttttctact aaatggaaaa gtacgacctc    660
actctattca aggagtgtat gaactaactg taaacggaat ttgtaataat aaaggagtag    720
tacaatactt tgataaatat aaactttaca ctaaaaaagc aagttcatat ctactatgga    780
```

```
aagaagtatc agaggatctt aaagatggaa aacatctttc tgaaagtact cgtctaatta    840
tgaaagaaaa ggtaataaaa atcaatagtt agaaatagta tataatctat cccacgggaa    900
taaagggtgt ggttctacat aattttata gttaatttaa aattttata ttccgacgcc      960 ttcagagcga ttrgaataaa taaaactaaa ttgcctctgg ggtcaacgtg taaaaacata   1020
ataactataa aaaagagcg aaattttatt aggcaggtgg tattttaata taatgtaaag   1080
acctaatatg ataaagagat attctctacc actactctag tccatgtcgt ataaatctgt   1140
gtaaccttta gaggaaaaca ggttttaagt atgtttatgc ccacaggcat aaagtgattc   1200
taaaaaatca tcggcaatac aagtgaaaac ggtcaacgta tattcgtatg aagaccgtcg   1260
gcagtctaaa ctgtcgctac agactgggtc acttgtgggt acctgaaatg gtgcttaatg   1320
tacagtcggc tttctctaat ggtaaaatca ttacacaagg ttattctctc tataagaggt   1380
cagaatagta cagggatttc taagagaact gataaattag aaatttggga aagtg         1435

<210> SEQ ID NO 35
<211> LENGTH: 30
<212> TYPE: DNA
<213> ORGANISM: Tilletia indica

<400> SEQUENCE: 35
gagatcctat tttatatcaa cacctattct                                      30

<210> SEQ ID NO 36
<211> LENGTH: 58
<212> TYPE: DNA
<213> ORGANISM: Tilletia indica

<400> SEQUENCE: 36
ggttcttcgg tcatcctgaa gtttatatcc tgattatacc aggatttggg atagtaag       58

<210> SEQ ID NO 37
<211> LENGTH: 1060
<212> TYPE: DNA
<213> ORGANISM: Tilletia horrida

<400> SEQUENCE: 37
gagatcctat tttatatcaa catctttttt ggttctttgg tcgaatatgg cccgatatac    60
ctatattcag aagggtatat atgaattaca ctgtatgctg gaaatatctg tttaatgtta   120
tttctactat catcataaga ggtattatta cgagcatatc ccgatatagt aaaaatgaaa   180
taacgaagat acaatcagca ggtaaccaac gacgctctat aagcagtcta gtaggaacca   240
cagagactat acgtgtaaca actttttcaa ccacttttgg acaatggcta gctggcgtta   300
ttgatggcga tggaagtcta caactgagta acaaggcta tacaagtctt gaaatcacta   360
tgggacttga agatcttcct ctacttcgtt atattcaaga taaacttgga ggatctatta   420
aaatgcgaac ggaagccaaa gcttatcgat atcgtctaca taataaaaga ggtatgatta   480
ctatgatcaa ctacataaac ggaaatattc gacattcatc acgacttaca caacttcacc   540
gagtatgtta acaacttcat atacctatca tggaaccgat tccactaacg aatgataatt   600
actggtttgc aggattttt gatgcagaag gtactattac gtttagtttc aagaatgaat   660
atcctcaact aagcatacga gtatctaata aaaacatgga agacgttcag tggtataaaa   720
atatatttgg aggctatatc tattttgata gtagtcaata tggtcattat caatggtcag   780
tgcaaagacg taatgatgtt ataagaatga aagatatttt caagaataaa tgtaaaagtc   840
ataaatcaaa ccgattttc cttatatcgg attattatca actttcagat ctaaaagcat   900
```

-continued

```
ataaaaaaga gagttaatat aataatctgt ggcactattt tgtccaaaag tgggacaaat    960
taagttgaag ataaagtcca ttttatttta ctgtgtaata tagtaaaaaa aagcatcccg   1020
aagtttatat tctaattata ccaggatttg ggatagtaag                         1060

<210> SEQ ID NO 38
<211> LENGTH: 972
<212> TYPE: DNA
<213> ORGANISM: Tilletia horrida

<400> SEQUENCE: 38
cgaatatggc ccgatatacc tatattcaga agggtatata tgaattacac tgtatgctgg     60
aaatatctgt ttaatgttat ttctactatc atcataagag gtattattac gagcatatcc    120
cgatatagta aaaatgaaat aacgaagata caatcagcag gtaaccaacg acgctctata    180
agcagtctag taggaaccac agagactata cgtgtaacaa ctttttcaac cacttttgga    240
caatggctag ctggcgttat tgatggcgat ggaagtctac aactgagtaa acaaggctat    300
acaagtcttg aaatcactat gggacttgaa gatcttcctc tacttcgtta tattcaagat    360
aaacttggag gatctattaa aatgcgaacg gaagccaaag cttatcgata tcgtctacat    420
aataaaagag gtatgattac tatgatcaac tacataaacg gaaatattcg acattcatca    480
cgacttacac aacttcaccg agtatgttaa caacttcata tacctatcat ggaaccgatt    540
ccactaacga atgataatta ctggtttgca ggatttttttg atgcagaagg tactattacg    600
tttagtttca agaatgaata tcctcaacta agcatacgag tatctaataa aaacatggaa    660
gacgttcagt ggtataaaaa tatatttgga ggctatatct attttgatag tagtcaatat    720
ggtcattatc aatggtcagt gcaaagacgt aatgatgtta taagaatgag aagatatttc    780
aagaataaat gtaaaagtca taaatcaaac cgatttttcc ttatatcgga ttattatcaa    840
ctttcagatc taaaagcata taaaaaagag agttaatata ataatctgtg gcactatttt    900
gtccaaaagt gggacaaatt aagttgaaga taaagtccat tttattttac tgtgtaatat    960
agtaaaaaaa ag                                                        972

<210> SEQ ID NO 39
<211> LENGTH: 41
<212> TYPE: DNA
<213> ORGANISM: Tilletia horrida

<400> SEQUENCE: 39
gagatcctat tttatatcaa catctttttt ggttctttgg t                          41

<210> SEQ ID NO 40
<211> LENGTH: 47
<212> TYPE: DNA
<213> ORGANISM: Tilletia horrida

<400> SEQUENCE: 40
catcccgaag tttatattct aattatacca ggatttggga tagtaag                    47

<210> SEQ ID NO 41
<211> LENGTH: 372
<212> TYPE: DNA
<213> ORGANISM: Tilletia tritici
<220> FEATURE:
<221> NAME/KEY: misc_feature
<222> LOCATION: (1)...(372)
<223> OTHER INFORMATION: n = A,T,C or G
```

<400> SEQUENCE: 41

```
gagatcctat tttatatcaa cacctgttct cactactaag actagttatt ctaattctat      60
ctatttattt tttccagctt acgcaggatc aacaaaccat aaataccttt tcctttcata     120
attttactga acaatttaaa accacatcat ttttcccttc taaacaagta cctacttctt     180
cttttctaga atggtttgta ggatttactg aaggagacgg cagttttgtt gtaagcactc     240
gtggtaactg tatgtttgtt attacacaat ctactaagga tattcaagtt cttcatttta     300
tctttgcttt acggctccgc ganttatata taataaaaaa gttcaagata aaccaggatt     360
tgggatagta ag                                                         372
```

<210> SEQ ID NO 42
<211> LENGTH: 291
<212> TYPE: DNA
<213> ORGANISM: Tilletia tritici

<400> SEQUENCE: 42

```
cactactaag actagttatt ctaattctat ctatttattt tttccagctt acgcaggatc      60
aacaaaccat aaataccttt tcctttcata attttactga acaatttaaa accacatcat     120
ttttcccttc taaacaagta cctacttctt cttttctaga atggtttgta ggatttactg     180
aaggagacgg cagttttgtt gtaagcactc gtggtaactg tatgtttgtt attacacaat     240
ctactaagga tattcaagtt cttcatttta tctttgcttt acggctccgc g              291
```

<210> SEQ ID NO 43
<211> LENGTH: 30
<212> TYPE: DNA
<213> ORGANISM: Tilletia tritici

<400> SEQUENCE: 43

```
gagatcctat tttatatcaa cacctgttct                                       30
```

<210> SEQ ID NO 44
<211> LENGTH: 51
<212> TYPE: DNA
<213> ORGANISM: Tilletia tritici
<220> FEATURE:
<221> NAME/KEY: misc_feature
<222> LOCATION: (1)...(51)
<223> OTHER INFORMATION: n = A,T,C or G

<400> SEQUENCE: 44

```
anttatatat aataaaaaag ttcaagataa accaggattt gggatagtaa g               51
```

<210> SEQ ID NO 45
<211> LENGTH: 1056
<212> TYPE: DNA
<213> ORGANISM: Candida tropicalis

<400> SEQUENCE: 45

```
gagatcctat tttatatcaa cacctcttct gattcttcgg tcaaggttgg ccctttgtaa      60
taccctatt acatacgcat tacactatat gctggaaact cctatgtaca tcgtacatag     120
cttacttaac tactctaggt atcagtctac tcctagcccc tagagtaaaa aggttaagag     180
atagtagcaa tactagcagt gatgcagcag akaaccaacg gttcatattc caagctatta     240
atgcctatga actcagtaga tatttcagag actacacgtg taactgtatc cccttctacg     300
gacccattcc atcaatgatt agctggtcta atcgatgcta atggtgcctt taaaatcact     360
cataaatcac aagtaaattg tgagataata gtgcctcaga acgaggaaag aatgttaaga     420
```

```
gttattcaag acaagtatgg tggttctatc aggcttagat caggtgatcg taccettcgt      480 tacagattac aagataaagc tagtgtaatc accttaatac aacatgttaa tggtaacctt      540
catactcctt aagattaagc caactacat cgggtatgtc ctctacttaa tatagaggct       600
aacatgccta tacctttaac catatttaat ggttgattta tgggctatttt tgatggtaaa     660 ggtaacatca gatgtagagt acctaatatc tacttaagtg ctacaggtaa agctgcagta     720
agtcttcaag gttttgttga tgttttttggt ggtgagatag tataccgtag agccagchat    780
ggttcatata catggaaact atcccgtcga cctagtgtgc tgttatttat gaggtatcag     840
amatgacata tatcacagtc aacammgcag cggagattgg gcttaatgag aaagtctatc    900
acttaattta catggagaaa gtggggatt taaaargatt ttctctgtta aagacatgag     960
twttattcca taataaatga aaataaatgc agaagatata gtccatacgc atcctgaggk    1020
ttatatcctg attataccag gatttgggat agtwag                               1056

<210> SEQ ID NO 46
<211> LENGTH: 968
<212> TYPE: DNA
<213> ORGANISM: Candida tropicalis

<400> SEQUENCE: 46
caaggttggc cctttgtaat acccttatta catacgcatt acactatatg ctggaaactc      60
ctatgtacat cgtacatagc ttacttaact actctaggta tcagtctact cctagccct     120 agagtaaaaa ggttaagaga tagtagcaat actagcagtg atgcagcaga kaaccaacgg   180
ttcatattcc aagctattaa tgcctatgaa ctcagtagat atttcagaga ctacacgtgt   240
aactgtatcc ccttctacgg acccattcca tcaatgatta gctggtctaa tcgatgctaa   300
tggtgccttt aaaatcactc ataaatcaca agtaaattgt gagataatag tgcctcagaa   360
cgaggaaaga atgttaagag ttattcaaga caagtatggt ggttctatca ggcttagatc   420
aggtgatcgt acccttcgtt acagattaca agataaagct agtgtaatca ccttaataca   480
acatgttaat ggtaaccttc atactccttt aagattaagc caactacatc gggtatgtcc   540
tctacttaat atagaggcta acatgcctat acctttaacc atatttaatg gttgatttat   600
gggctatttt gatggtaaag gtaacatcag atgtagagta cctaatatct acttaagtgc   660
tacaggtaaa gctgcagtaa gtcttcaagg ttttgttgat gttttggtg gtgagatagt   720 ataccgtaga gccagchatg gttcatatac atggaaacta tcccgtcgac ctagtgtgct   780
gttatttatg aggtatcaga matgacatat atcacagtca acammgcagc ggagattggg   840
cttaatgaga aagtctatca cttaatttac atggagaaaa gtggggattt aaaargattt   900
tctctgttaa agacatgagt wttattccat aataaatgaa aataaatgca gaagatatag   960
tccatacg                                                              968

<210> SEQ ID NO 47
<211> LENGTH: 41
<212> TYPE: DNA
<213> ORGANISM: Candida tropicalis

<400> SEQUENCE: 47
gagatcctat tttatatcaa cacctcttct gattcttcgg t                          41

<210> SEQ ID NO 48
<211> LENGTH: 47
<212> TYPE: DNA
```

<213> ORGANISM: Candida tropicalis

<400> SEQUENCE: 48
catcctgagg kttatatcct gattatacca ggatttggga tagtwag          47

<210> SEQ ID NO 49
<211> LENGTH: 234
<212> TYPE: PRT
<213> ORGANISM: Candida tropicalis
<220> FEATURE:
<221> NAME/KEY: VARIANT
<222> LOCATION: (1)...(234)
<223> OTHER INFORMATION: Xaa = Any Amino Acid

<400> SEQUENCE: 49

```
Met Gln Gln Xaa Thr Asn Gly Ser Tyr Ser Lys Thr Leu Met Pro Met
 1               5                  10                  15

Asn Ser Val Asp Ile Ser Glu Thr Thr Arg Val Thr Val Ser Pro Ser
            20                  25                  30

Thr Asp Pro Phe His Gln Trp Leu Ala Gly Thr Ile Asp Ala Asn Gly
        35                  40                  45

Ala Phe Lys Ile Thr His Lys Ser Gln Val Asn Cys Glu Met Met Val
 50                  55                  60

Pro Gln Asn Glu Glu Arg Met Leu Arg Val Ile Gln Asp Lys Tyr Gly
 65                  70                  75                  80

Gly Ser Ile Arg Thr Arg Ser Gly Asp Arg Thr Thr Arg Tyr Arg Leu
                85                  90                  95

Gln Asp Lys Ala Ser Val Ile Thr Leu Met Gln His Val Asn Gly Asn
            100                 105                 110

Thr His Thr Pro Leu Arg Leu Ser Gln Thr His Arg Val Cys Pro Thr
        115                 120                 125

Thr Asn Met Glu Ala Asn Met Pro Met Pro Leu Thr Met Phe Asn Gly
130                 135                 140

Trp Phe Met Gly Tyr Phe Asp Gly Lys Gly Asn Ile Arg Cys Arg Val
145                 150                 155                 160

Pro Asn Ile Tyr Leu Ser Ala Thr Gly Lys Ala Ala Val Ser Thr Gln
                165                 170                 175

Gly Phe Val Asp Val Phe Gly Gly Glu Met Val Tyr Arg Arg Ala Ser
            180                 185                 190

Xaa Gly Ser Tyr Thr Trp Lys Thr Ser Arg Arg Pro Ser Val Thr Leu
        195                 200                 205

Phe Met Arg Tyr Gln Xaa Trp His Met Ser Gln Ser Thr Xaa Gln Arg
210                 215                 220

Arg Leu Gly Leu Met Arg Lys Ser Ile Thr
225                 230
```

<210> SEQ ID NO 50
<211> LENGTH: 156
<212> TYPE: PRT
<213> ORGANISM: Tilletia horrida

<400> SEQUENCE: 50

```
Met Asn Tyr Thr Val Cys Trp Lys Tyr Thr Phe Asn Val Ile Ser Thr
 1               5                  10                  15

Ile Ile Met Arg Gly Ile Ile Thr Ser Met Ser Arg Tyr Ser Lys Asn
            20                  25                  30

Glu Met Thr Lys Met Gln Ser Ala Gly Asn Gln Arg Arg Ser Met Ser
        35                  40                  45
```

-continued

Ser Thr Val Gly Thr Thr Glu Thr Met Arg Val Thr Thr Phe Ser Thr
 50                  55                  60

Thr Phe Gly Gln Trp Thr Ala Gly Val Ile Asp Gly Asp Gly Ser Thr
 65                  70                  75                  80

Gln Thr Ser Lys Gln Gly Tyr Thr Ser Thr Glu Ile Thr Met Gly Thr
                 85                  90                  95

Glu Asp Thr Pro Thr Thr Arg Tyr Ile Gln Asp Lys Thr Gly Gly Ser
            100                 105                 110

Ile Lys Met Arg Thr Glu Ala Lys Ala Tyr Arg Tyr Arg Thr His Asn
        115                 120                 125

Lys Arg Gly Met Ile Thr Met Ile Asn Tyr Met Asn Gly Asn Ile Arg
    130                 135                 140

His Ser Ser Arg Thr Thr Gln Thr His Arg Val Cys
145                 150                 155

<210> SEQ ID NO 51
<211> LENGTH: 115
<212> TYPE: PRT
<213> ORGANISM: Tilletia horrida

<400> SEQUENCE: 51

Met Glu Pro Ile Pro Thr Thr Asn Asp Asn Tyr Trp Phe Ala Gly Phe
 1               5                  10                  15

Phe Asp Ala Glu Gly Thr Ile Thr Phe Ser Phe Lys Asn Glu Tyr Pro
            20                  25                  30

Gln Thr Ser Met Arg Val Ser Asn Lys Asn Met Glu Asp Val Gln Trp
        35                  40                  45

Tyr Lys Asn Met Phe Gly Gly Tyr Ile Tyr Phe Asp Ser Ser Gln Tyr
 50                  55                  60

Gly His Tyr Gln Trp Ser Val Gln Arg Arg Asn Asp Val Met Arg Met
 65                  70                  75                  80

Arg Arg Tyr Phe Lys Asn Lys Cys Lys Ser His Lys Ser Asn Arg Phe
                 85                  90                  95

Phe Thr Met Ser Asp Tyr Tyr Gln Thr Ser Asp Thr Lys Ala Tyr Lys
            100                 105                 110

Lys Glu Ser
        115

<210> SEQ ID NO 52
<211> LENGTH: 1547
<212> TYPE: DNA
<213> ORGANISM: Lycoperdon pyriforme
<220> FEATURE:
<221> NAME/KEY: misc_feature
<222> LOCATION: (1)...(1547)
<223> OTHER INFORMATION: n = A,T,C or G

<400> SEQUENCE: 52
gtatgatagg gtttaggacc atattaattt tatatttgaa gacctactgg ttttttgggt      60
agggattttt gggatctaaa taatcgagag agatcccggg tacatgataa catccgacct     120
acgaattatc gggtcatccg gtccatctaa atccgagcgc tttcacggat ttgatgacga     180
ccgaaaccga caaccttgga tttttggatt agagtatttc tcgtgttatc ggaacacatt     240
atattcctta gctgacatgt aattcgtgga aaagtccgtg ggtgttcact gggtcagaca     300
tcgctatcaa atttgatggc tgccagaacc aagctcgttt gcaactggca aaagtgaaca     360
tagcggttac ttgttaacaa gtaggaatgc ggacagcccc attcgtataa taatcgacga     420

```
gacgacgttg tttccgattc gacaaaaaga gatttctaat gtgttggaca tattatacct      480
gatcttatca ccatatttat aataagtgag attgtccaga aatcttaatt ttatctgtgg      540
acggataatc tcaaagtgtt gaacagagat tagatcaatc ggaccatcca ttctctataa      600
tgtaacttgg tgaaggaaat aagggcaacc caacatgtga ttaagtacaa taattatcat      660
cgacgaaact gaaagtcacg acgagctctg agaccattgt ctacaagagg aaattcctat      720
cttcgtactt gaagagcggt ataaccatg cttaatcgaa aaaccaaac attgcctact       780 catagcttta taaacttatg agcaaggtgc aaagctcgtg gtaactgtca attaagcata      840
tgagggtcaa atctcactaa tgcttgttgt ggaggttatt caaatcattc gacacagtca      900
tgtcaatcta attgaagagg aaaaacacga tcttctttag ccttagatat gcgcaaactc      960
aatggattat tactcgttaa cttcgttgga agtcgcagac attttggacg attggttttt     1020
agcacatacg aatcagatca tcctcattag tcactgccaa attcaagatg acgaactcat     1080
cggtttctgt tactagaaaa caatttccga agttctttat ttcgtttcga tctaacaaat     1140
caacactttt aatctaaagg taatttatct cgttgatcgt cacgtntgtg accgcaacag     1200
aagttgatgt tttgctgatc aagcaacagg aacaaattaa tgtgctggtt ttggatctca     1260
agcaacttat atgaattctt gaacatctag ttcacatgaa acacattagt gcttttatcg     1320
acaaggtgct gacaactaat atttcgatgg cagaggaagg cttttagggt gatcggttag     1380 attttttccta actgatcctc ggaatcgcaa tccttttgca aatgacattt cacagttttt     1440
acacggttta acctttccga gcgccctcga acagcttaag aatcgatgat ctccttatca     1500
catgttacaa aaacaattct tattcacaac tatattttat cctagag                   1547
```

<210> SEQ ID NO 53
<211> LENGTH: 203
<212> TYPE: PRT
<213> ORGANISM: Lycoperdon pyriforme
<220> FEATURE:
<221> NAME/KEY: VARIANT
<222> LOCATION: (1)...(203)
<223> OTHER INFORMATION: Xaa = Any Amino Acid

<400> SEQUENCE: 53

```
Met Leu Leu Met Val Ala Ala Leu Thr Phe Ser Ala Ala Arg Asp Ser
  1               5                  10                  15

Gly Asn Arg Cys Ser Pro Leu Arg Met Glu Ala Trp Thr Ser Arg His
             20                  25                  30

Ile Trp Tyr Glu Leu Ala Phe Leu Val Cys Asn Gly Trp Val Ser Lys
         35                  40                  45

Tyr Leu Asn Thr Arg Ser Thr Phe Arg Ala Pro Leu Thr Val Asn Ser
     50                  55                  60

Tyr Thr Pro Ser Leu Glu Trp Leu Arg Thr Thr Pro Pro Met Ser Leu
 65                  70                  75                  80

Val Ser Cys Val Ser Thr Val Arg Leu Thr Ser Pro Phe Cys Ala Arg
                 85                  90                  95

Arg Asn Arg Asn Thr Tyr Ala Phe Glu Leu Pro Asn Asn Glu Gln Leu
            100                 105                 110

Lys Gln Pro Ser Ala Ser Val Lys Pro Ala Asn Gln Lys Ser Cys Met
        115                 120                 125

Thr Ser Thr Val Gly Val Ile Ser Asp Gly Leu Ser Ser Thr Ala Trp
    130                 135                 140

Val Ala Lys Asp Asn Asp Thr Leu Leu Lys Ala Ser Arg Asn Lys Ala
```

```
                145                 150                 155                 160
Lys Thr Asp Cys Leu Val Val Lys Ile Arg Phe Pro Leu Asn Arg Ala
                165                 170                 175

Thr Ser Ser Ala Xaa Thr Gly Val Val Phe Asn Tyr Lys Thr Thr Ser
                180                 185                 190

Ser Leu Ser Leu Phe Asn Tyr Thr Thr Lys Thr
        195                 200

<210> SEQ ID NO 54
<211> LENGTH: 225
<212> TYPE: PRT
<213> ORGANISM: Tilletia indica

<400> SEQUENCE: 54

Met Ser Thr Arg Gly Asn Cys Met Phe Val Ile Thr Gln Ser Thr Lys
  1               5                  10                  15

Asp Ile Gln Val Thr His Phe Ile Gln Asp Lys Thr Gly Phe Gly Arg
                 20                  25                  30

Val Ile Lys Gln Gly His Ser Thr Ser Arg Phe Ile Val Gln Asp Asn
             35                  40                  45

Lys Asn Thr Tyr Thr Thr Thr His Thr Phe Asn Gly Asn Thr Val Thr
 50                  55                  60

Pro Thr Lys Met Glu Ser Phe Lys Lys Phe Met Glu Met Phe Ile Lys
 65                  70                  75                  80

Asn Ser Ser Asn Tyr Ser Ile Thr Pro Ile Ser Val Trp Arg Thr Thr
                 85                  90                  95

Pro Ser Cys Asn Asp Ala Trp Ile Ser Gly Phe Thr Asp Ala Glu Gly
                100                 105                 110

Cys Phe Thr Cys Ser Thr Thr Gly Asn Ser Thr Ala Tyr Arg Phe Arg
            115                 120                 125

Phe Met Thr Ser Gln Lys Asn Glu Lys Asn Lys Cys Val Thr Asp His
        130                 135                 140

Ile Ala Phe Thr Thr Asn Gly Lys Val Arg Pro His Ser Ile Gln Gly
145                 150                 155                 160

Val Tyr Glu Thr Thr Val Asn Gly Ile Cys Asn Asn Lys Gly Val Val
                165                 170                 175

Gln Tyr Phe Asp Lys Tyr Lys Thr Tyr Thr Lys Lys Ala Ser Ser Tyr
            180                 185                 190

Thr Thr Trp Lys Glu Val Ser Glu Asp Thr Lys Asp Gly Lys His Thr
        195                 200                 205

Ser Glu Ser Thr Arg Thr Ile Met Lys Glu Lys Val Met Lys Ile Asn
    210                 215                 220

Ser
225

<210> SEQ ID NO 55
<211> LENGTH: 1481
<212> TYPE: DNA
<213> ORGANISM: Aspergillus niger

<400> SEQUENCE: 55
gagatcctat tttatatcaa catcttttct caagagatat ttaattaat tgtttaatat    60 taacaattct agcttcaata gtaaagatta taaatcaaa tttaagtttt aaatttaatt   120
atagtacttt cataaataaa tttrattttt caaatttta tataaaattt tctaattatt   180
tacctaataa tacttacct tcagaaaaat tcttgacttg atttatagga ttcacagaag   240
```

-continued

```
gtgagggtc atttatagta aataatagag gtgatctttg ttttgttatt acacaaaaaa      300
ctatagatat tgaaatatta gaatttataa agaaacttt aggttttggt aaagtaattc      360
aacaatctaa attaactagt agatatgtta cacaaaacaa aaagaaata gaaatactta      420 ttcatttgtt taatggtaat cttatattac caagtagaaa gataaaattt gaaaatttca     480
ttaaaggatt taatatttga ataggtaaag gtagaataaa attagatcct gttgaattaa     540
aacataattt tattttacct agtttaaata atagttgatt ggcaggtttt actgatgggg     600
aaggctgtyt tacttgttct ataggtaaag acaaggatt tagttttaat tttaatattg      660 ctcaaaatg agaggaaaat attgaagtat tacaacatct ttgtacttta tttaatggag      720
gaatagtctc aaaacatagt gtggataatg taaatgaatt tagaatagga ggattaaaaa     780
attgtaaaaa tatatttccc tattttgata cttatacatt attaactaaa aaatctacta     840
gttatatttt atgaaaagaa atatatgaag atttgttaaa aaaatatcat ttagacccaa     900 ttaaagggt agagatgatt gaaaaagcta gattgataaa taaaattaat taattaaaat     960
attagggaaa aaagtaaag gtttaacgtg caagttttga agctcttagg acagatgtaa    1020
aaggatataa gatccaaaag agcaaatatt ctataatgaa tataccttat acttagttaa    1080
tgtttagtta ttactacttg caactcttaa gtgtaacgta tatataattt ggtatatatt    1140
gttatactta tcaattaata tataattgat aaaaggaaaa gttagtataa acattagcga    1200
tactagtgtt aacggtcaat aaattttcat gtttaaagac cgtcggttat ttaagtgacc    1260
gctacagact ggttcactgg taggtggctg aaatgctgct taatgtacag tcggttcctt    1320 ccataatttta tatatgcaca agcccagaat tatataatta ctggtacctg gatttaataa    1380
atgaacatca atatattgat gagaagttaa atttgaagga atggattctt cggacatccg    1440
gaagtttaca tcttaattat accaggattt gggatagtaa g                          1481
```

<210> SEQ ID NO 56
<211> LENGTH: 1393
<212> TYPE: DNA
<213> ORGANISM: Aspergillus niger

<400> SEQUENCE: 56

```
caagagatat tttaattaat tgtttaatat taacaattct agcttcaata gtaaagatta     60
ataaatcaaa tttaagtttt aaatttaatt atagtacttt cataaataaa ttttatttt     120 caaattttta tataaaattt tctaattatt tacctaataa tactttacct tcagaaaaat    180
tcttgacttg atttatagga ttcacagaag gtgagggtc atttatagta aataatagag     240
gtgatctttg ttttgttatt acacaaaaaa ctatagatat tgaaatatta gaatttataa     300 agaaacttt aggttttggt aaagtaattc aacaatctaa attaactagt agatatgtta     360
cacaaaacaa aaagaaata gaaatactta ttcatttgtt taatggtaat cttatattac     420
caagtagaaa gataaaattt gaaaatttca ttaaaggatt taatatttga ataggtaaag     480
gtagaataaa attagatcct gttgaattaa aacataattt tattttacct agtttaaata     540
atagttgatt ggcaggtttt actgatgggg aaggctgtyt tacttgttct ataggtaaag     600 acaaggatt tagttttaat tttaatattg ctcaaaatg agaggaaaat attgaagtat      660
tacaacatct ttgtacttta tttaatggag gaatagtctc aaaacatagt gtggataatg     720
taaatgaatt tagaatagga ggattaaaaa attgtaaaaa tatatttccc tattttgata     780
cttatacatt attaactaaa aaatctacta gttatatttt atgaaaagaa atatatgaag     840
```

```
atttgttaaa aaaatatcat ttagacccaa ttaaaagggt agagatgatt gaaaaagcta      900
gattgataaa taaaattaat taattaaaat attagggaaa aaaagtaaag gtttaacgtg      960
caagttttga agctcttagg acagatgtaa aaggatataa gatccaaaag agcaaatatt     1020
ctataatgaa tataccttat acttagttaa tgtttagtta ttactacttg caactcttaa     1080
gtgtaacgta tatataattt ggtatatatt gttatactta tcaattaata tataattgat     1140
aaaaggaaaa gttagtataa acattagcga tactagtgtt aacggtcaat aaattttcat     1200
gtttaaagac cgtcggttat ttaagtgacc gctacagact ggttcactgg taggtggctg     1260
aaatgctgct taatgtacag tcggttcctt ccatatttta tatatgcaca agcccagaat     1320
tatataatta ctggtacctg gatttaataa atgaacatca atatattgat gagaagttaa     1380
atttgaagga atg                                                        1393
```

<210> SEQ ID NO 57
<211> LENGTH: 30
<212> TYPE: DNA
<213> ORGANISM: Aspergillus niger

<400> SEQUENCE: 57

```
gagatcctat tttatatcaa catcttttct                                        30
```

<210> SEQ ID NO 58
<211> LENGTH: 58
<212> TYPE: DNA
<213> ORGANISM: Aspergillus niger

<400> SEQUENCE: 58

```
gattcttcgg acatccggaa gtttacatct taattatacc aggatttggg atagtaag        58
```

<210> SEQ ID NO 59
<211> LENGTH: 316
<212> TYPE: PRT
<213> ORGANISM: Aspergillus flavus
<220> FEATURE:
<221> NAME/KEY: VARIANT
<222> LOCATION: (1)...(316)
<223> OTHER INFORMATION: Xaa = Any Amino Acid

<400> SEQUENCE: 59

```
Asp Pro Ile Leu Tyr Gln His Leu Phe Ser Arg Asp Ile Leu Ile Asn
 1               5                  10                  15

Cys Leu Ile Leu Thr Ile Leu Ala Ser Ile Val Lys Ile Asn Lys Ser
            20                  25                  30

Asn Leu Ser Phe Lys Phe Asn Tyr Ser Thr Phe Ile Asn Lys Phe Xaa
        35                  40                  45

Phe Ser Asn Phe Tyr Ile Lys Phe Ser Asn Tyr Leu Pro Asn Asn Thr
    50                  55                  60

Leu Pro Ser Glu Lys Phe Leu Thr Trp Phe Ile Gly Phe Thr Glu Gly
65                  70                  75                  80

Glu Gly Ser Phe Ile Val Asn Asn Arg Gly Asp Leu Cys Phe Val Ile
                85                  90                  95

Thr Gln Lys Thr Ile Asp Ile Glu Ile Leu Glu Phe Ile Lys Glu Thr
            100                 105                 110

Leu Gly Phe Gly Lys Val Ile Gln Gln Ser Lys Leu Thr Ser Arg Tyr
        115                 120                 125

Val Thr Gln Asn Lys Lys Glu Ile Glu Ile Leu Ile His Leu Phe Asn
    130                 135                 140
```

-continued

```
Gly Asn Leu Ile Leu Pro Ser Arg Lys Ile Lys Phe Glu Asn Phe Ile
145                 150                 155                 160

Lys Gly Phe Asn Ile Trp Ile Gly Lys Gly Arg Ile Lys Leu Asp Pro
                165             170                 175

Val Glu Leu Lys His Asn Phe Ile Leu Pro Ser Leu Asn Asn Ser Trp
                180             185                 190

Leu Ala Gly Phe Thr Asp Gly Glu Gly Cys Xaa Thr Cys Ser Ile Gly
        195                 200             205

Lys Asp Lys Gly Phe Ser Phe Asn Phe Asn Ile Ala Gln Lys Trp Glu
        210             215             220

Glu Asn Ile Glu Val Leu Gln His Leu Cys Thr Leu Phe Asn Gly Gly
225                 230             235                 240

Ile Val Ser Lys His Ser Val Asp Asn Val Asn Glu Phe Arg Ile Gly
                245             250                 255

Gly Leu Lys Asn Cys Lys Asn Ile Phe Pro Tyr Phe Asp Thr Tyr Thr
                260             265                 270

Leu Leu Thr Lys Lys Ser Thr Ser Tyr Ile Leu Trp Lys Glu Ile Tyr
            275             280              285

Glu Asp Leu Leu Lys Lys Tyr His Leu Asp Pro Ile Lys Arg Val Glu
    290             295             300

Met Ile Glu Lys Ala Arg Leu Ile Asn Lys Ile Asn
305             310             315
```